US007563883B2

(12) United States Patent
Angov et al.

(10) Patent No.: US 7,563,883 B2
(45) Date of Patent: Jul. 21, 2009

(54) **RECOMBINANT *P. FALCIPARUM* MEROZOITE PROTEIN-1₄₂ VACCINE**

(75) Inventors: Evelina Angov, Bethesda, MD (US); Jeffrey A. Lyon, Silver Spring, MD (US); Christian Asare Darko, Silver Spring, MD (US); Joe D. Cohen, Brussels (BE)

(73) Assignee: The United States of America as represented by the Secretary of the Army, Washington, DC (US)

( * ) Notice: Subject to any disclaimer, the term of this patent is extended or adjusted under 35 U.S.C. 154(b) by 0 days.

(21) Appl. No.: 11/889,578

(22) Filed: Aug. 14, 2007

(65) Prior Publication Data

US 2008/0075741 A1 Mar. 27, 2008

Related U.S. Application Data

(62) Division of application No. 10/404,667, filed on Apr. 1, 2003, now Pat. No. 7,256,281.

(60) Provisional application No. 60/379,688, filed on May 9, 2002, provisional application No. 60/359,741, filed on Apr. 1, 2002.

(51) Int. Cl.
*C07H 21/04* (2006.01)
*C12P 21/04* (2006.01)
*C07K 14/295* (2006.01)
*A61K 39/015* (2006.01)

(52) U.S. Cl. .................. 536/23.7; 536/23.1; 435/69.1; 435/69.7; 435/320.1; 424/272.1; 530/350

(58) Field of Classification Search ....................... None
See application file for complete search history.

(56) References Cited

U.S. PATENT DOCUMENTS

| 4,978,621 | A | 12/1990 | Ardeshir et al. |
| 6,551,586 | B1 | 4/2003 | Davidson et al. |
| 6,855,322 | B2 * | 2/2005 | Lyon et al. ............... 424/268.1 |

FOREIGN PATENT DOCUMENTS

| CA | 2245727 | 8/1997 |
| WO | WO-01/34188 A1 | 5/2001 |

OTHER PUBLICATIONS

Kumar et al, 1995, Molecular Medicine 1: (3) 325-332.*
Short Protocols in Molecular Biology Ed: Ausubel Publisher: John Wiley, pp. 10-59, 16-31, 16-32, 16-33 and 16-34.*
Office Action dated Sep. 28, 2007; CA Application No. 2,480,786.
Stowers, A., et al.; "A Recombinant Vaccine Expressed in the Milk of Transgenic Mice Protects *Aotus* Monkeys from a Lethal Challenge with *Plasmodium falciparum*"; PNAS; Jan. 8, 2002; vol. 99; No. 1; pp. 339-344.
Stowers, A., et al.; Efficacy of Two Alternate Vaccines Based on *Plasmodium falciparum* Merozoite Surface Protein 1 in an *Aotus* Challenge Trial; Infection and Immunity; Mar. 2001; vol. 69, No. 3; pp. 1536-1546.
Angov et al., "Process Development for Clinical Grade *Plasmodium falciparum* MSP1/42 (3D7) Expressed in *E. coli*", American Journal of Tropical Medicine & Hygiene, Lawrence, Nov. 28, 1999, p. 207, vol. 61, No. 3.
Dutta et al., "Purification, Characterization, and Immunogenicity of a Disulfide Cross-Linked Plasmodium Vivax Vaccine Candidate Antigen, Merozoite Surface Protein 1, Expressed in *Escherichia coli*", Infection and Immunity, American Society for Microbiology, Sep. 2001, pp. 5464-5470, vol. 69, No. 9.
Pang et al., "In Vivo Expression and Immunological Studies of the 42-Kilodalton Carboxyl-Terminal Processing Fragment of *Plasmodium falciparum* Merozoite Surface Protein 1 in the Baculovirus-Silkworm System", Infection and Immunity, Jun. 2002, pp. 2772-2779, vol. 70, No. 6.
Qian et al., "Inducible Expression of MSP1 Gene of *Plasmodium falciparum* by a Tetracycline-Controlled Promoter", Chinese Journal of Parasitology & Parasitic Diseases, 2000, pp. 193-196, vol. 18, No. 4. (with English Abstract).
Weiqing et al., "Vaccine Candidate MSP-1 from *Plasmodium falciparum*: A Redesigned 4917 BP Polynucleotide Enables Synthesis and Isolation of Full-Length Protein from *Escherichia coli* and Mammalian Cells", Nucleic Acids Research, 1999, pp. 1094-1103, vol. 27, No. 4.
Kumar, S. et al., 1995. Immunogenicity and In Vivo Efficacy of Recombinant *Plasmodium falciparum* Merozoite Surface Protein-1 in Aotus Monkeys. Molecular Medicine 1, 325-332.
Kumar, S. et al., 2002. A DNA Vaccine Encoding the 42KDA C-Terminus of Merozoite Surface Protein 1 of *Plasmodium falciparum* Induces Antibody, Interferon-Y and Cytotoxic T Cell Responses in Rhesus Monkey: Immuno-Stimulatory Effects of Granulocyte Macrophage-Colony Stimulating Factor. Immunology Letters 81, 13-24.
Angov, E. et al/, 2003. Development and Pre-Clinical Analysis of a *Plasmodium faciparum* Merozoite Surface Protein-1₄₂ ₇Malaria Vaccine. Molecular & Biochemical Parasitology 128, 195-204.
Genton, B. et al., 2000. Safety and Immunogenicity of a Three-Component Blood-Stage Malaria Vaccine in Adults Living in an Endemic Area of Papua New Guinea. Vaccine 18, 2504-2511.
Chang, S. P. et al., 1996. A Recombinant Baculovirus 42-Kilodalton C-Terminal Fragment of *Plasmodium falciparum* Merozoite Surface Protein 1 Protects Aotus Monkeys Against Malaria. Infection and Immunity 64, 253-261.
Genton, B. et al., 2002. A Recombinant Blood-Stage Malaria Vaccine Reduces *Plasmodium falciparum* Density and Exerts Selective Pressure on Parasite Populations in a Phrase 1-2B Trial in Papua New Guinea. J. Of Infectious Diseases 185, 820-827.
Longacre, S., et al., Mol. Biochem. Parasitol. 64(2); 191-205, Apr. 1994.

\* cited by examiner

*Primary Examiner*—Robert B Mondesi
*Assistant Examiner*—Padma V Baskar
(74) *Attorney, Agent, or Firm*—Elizabeth Arwine

(57) ABSTRACT

In this application is described the expression and purification of a recombinant *Plasmodium falciparum* (FVO) MSP-1₄₂. The method of the present invention produces a highly purified protein that retains folding and disulfide bridging of the native molecule. The recombinant MSP-1₄₂ is useful as a diagnostic reagent, for use in antibody production, and as a vaccine.

4 Claims, 9 Drawing Sheets

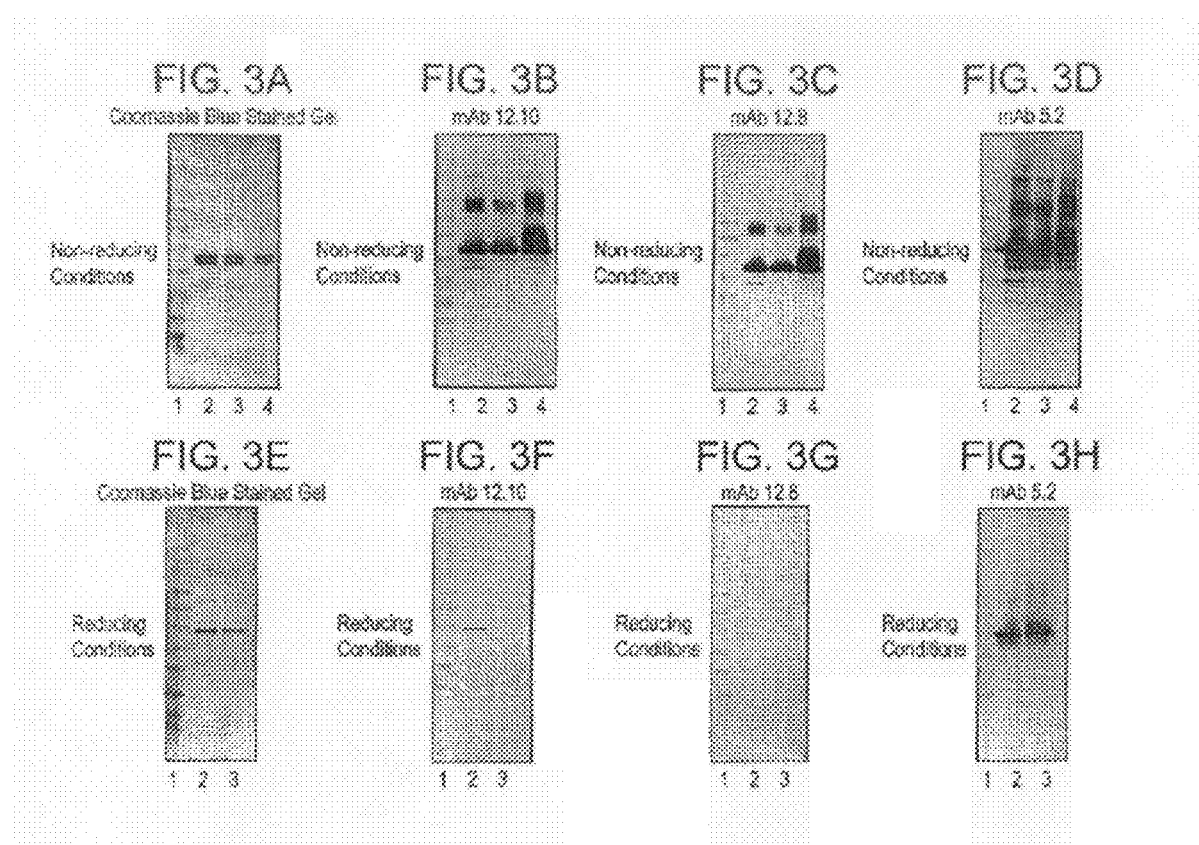

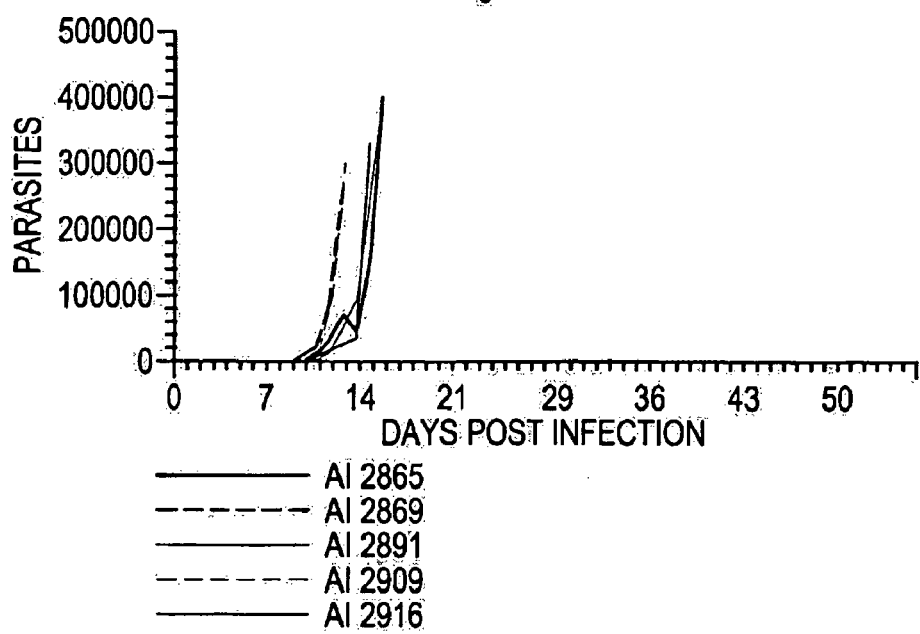
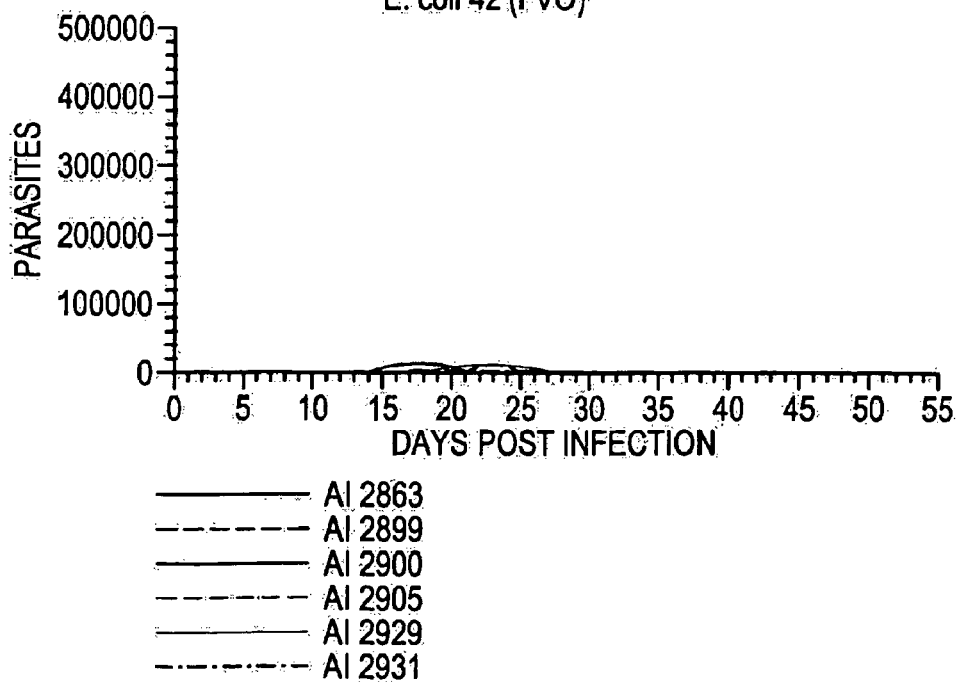

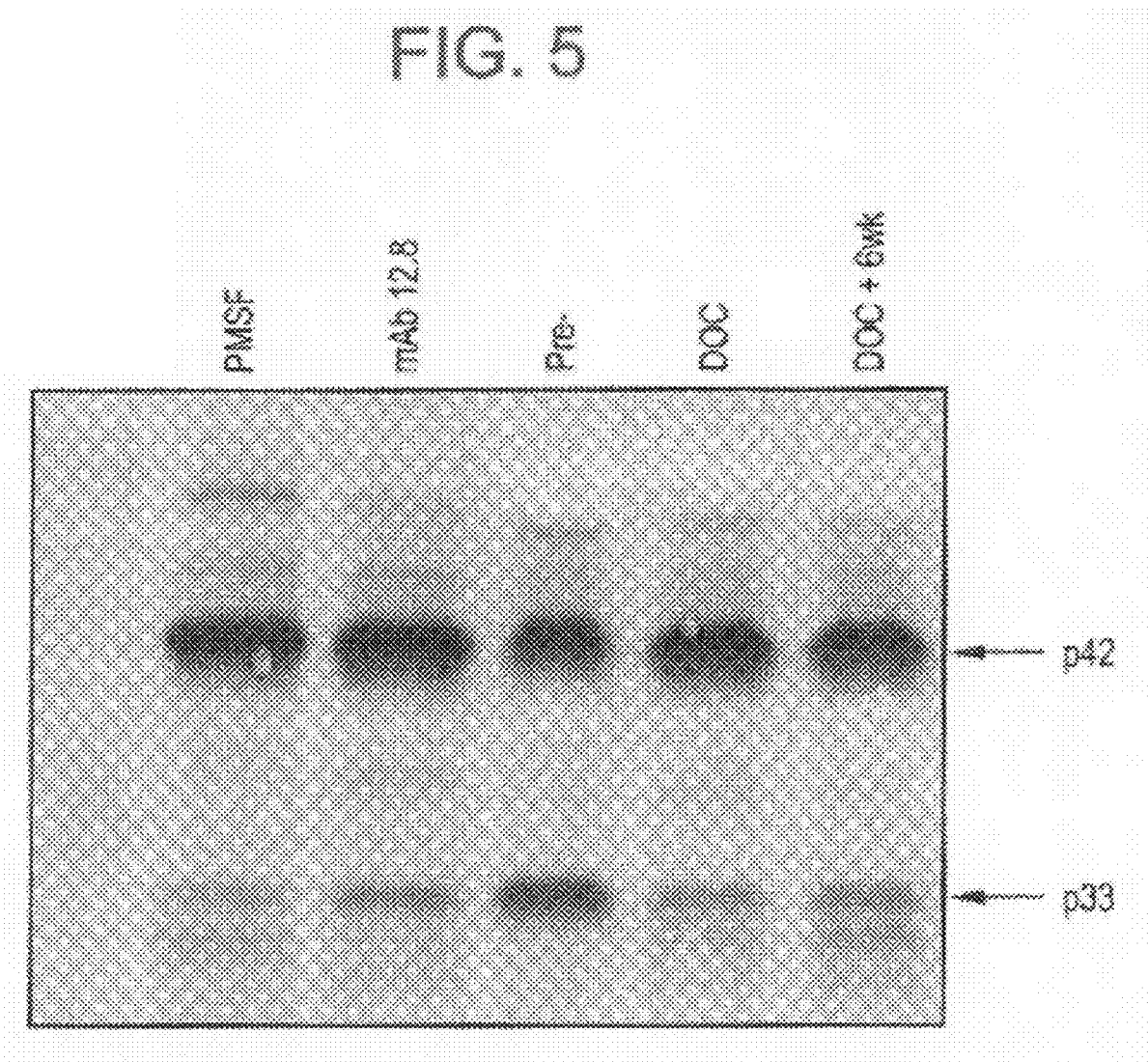

RECOMBINANT *P. FALCIPARUM* MEROZOITE PROTEIN-$1_{42}$ VACCINE

CROSS REFERENCE TO RELATED APPLICATIONS

This application is a divisional of U.S. application Ser. No. 10/404,667, filed Apr. 1, 2003, which claims the benefit of U.S. Provisional Application Ser. No. 60/264,535, filed Jan. 29, 2001 and Provisional Application Ser. No. 60/347,564 filed Oct. 26, 2001, all of which are hereby incorporated in their entirety by reference.

*Plasmodium falciparum* is the leading cause of malaria morbidity and mortality. The World Health Organization estimates that approximately 200 million cases of malaria are reported yearly, with 3 million deaths (World Health Organization, 1997, Wkly. Epidemiol. Rec. 72:269-276). Although, in the past, efforts have been made to develop effective controls against the mosquito vector using aggressive applications of pesticides, these efforts ultimately led to the development of pesticide resistance. Similarly, efforts at treatment of the disease through anti-parasitic drugs led to parasite drug-resistance. As the anti-vector and anti-parasite-approaches failed, efforts became focused on malaria vaccine development as an effective and inexpensive alternative approach.

However, the complex parasitic life cycle has further confounded the efforts to develop efficacious vaccines for malaria. The parasite's life cycle is divided between the mosquito-insect host and the human host. While in the human host, it passes through several developmental stages in different organellar environments, i.e. the liver stage, the red blood stage. Although conceptually simple, in reality the problems that must be considered when designing subunit vaccines for malaria are great. Antigen diversity is a characteristic that must be taken into account and includes a high degree of developmental stage specificity, antigenic variation and antigen polymorphism. Vaccine candidates have been identified from each of the parasite's developmental stages. The major merozoite surface protein-1, MSP-1, is among the leading erythrocytic stage vaccine candidates (Diggs, et al, 1993, Parasitol. Today 9: 300-302). The objective of erythrocytic stage vaccines is to diminish the level of parasitemia in the bloodstream and thus reduce the severity of disease.

Although the MSP-1 molecule has been studied extensively, its function is not fully understood. There is evidence that MSP-1 binds to erythrocytes and may have a role in erythrocyte invasion (Perkins and Rocco, 1988, J. Immunol. 141, 3190-3196; Holder, A. A., 1994, Parasitology 108 (Suppl.) S5-18).

MSP-1 is secreted as a membrane-anchored (Haldar et al., 1985, J. Biol. Chem. 260, 4969-4974) 195 kDa precursor that is proteolytically processed to products with nominal molecular masses of 83, 28-30, 38-45, and 42 kDa during merozoite development (Holder and Freeman, 1984, Phils Trans R. Soc. Lond B. Bio. Sci. 307, 171-177; Lyon et al., 1987, J. Immunol, 138, 895-901; Holder et al., 1987, Parasitology 94, 199-208). These protein fragments form a non-covalent complex on the surface of merozoites (McBride and Heidrich, 1987, Parasitology 23, 71-84; Lyon, et al., 1987, supra) that remain attached to the merozoite surface through the C-terminal 42 kDa fragment (MSP-$1_{42}$). At the time of erythrocyte invasion MSP-$1_{42}$ is processed further to a 33 kDa fragment and a 19 kDa C-terminal fragment (MSP-$1_{19}$) (Blackman, et al., 1991, Mol. Biochem. Parasitol. 49, 35-44) which is bound to the merozoite surface through an N-glycosylphosphatidyl inositol anchor (GPI) (Haldar, et al., 1985, supra). This second proteolytic cleavage event results in the shedding of the non-covalent associated protein complex from the merozoite surface during invasion. During the invasion process, MSP-$1_{19}$ is present on ring forms in the newly invaded erythrocyte (Blackman, et al., 1990, J. Exp. Med. 172, 379-382). The apparent structure of MSP-$1_{19}$ is complex, containing 12 cysteines within a span of 100 amino acid residues, and is arranged as two tandem domains that are homologous with epidermal growth factor (EGF) (Blackman, et al., 1991, supra; Morgan et al., 2000, J. Biomol. NMR 17, 337-347). Each putative EGF-domain contains six cysteine residues that would form three disulfide bridges per domain, which force the assembly of several well-defined discontinuous epitopes (Farley and Long, 1995, Exp. Parasitol. 80, 328-332; McBride and Heidrich, 1987, supra; Uthaipibull et al, 2001, J. Mol. Biol. 307, 1381-1394).

Because age-dependent development of immunity to malaria is due, at least in part, to antibody against erythrocytic stage parasites (Cohen, S. et al., 1964, Nature 192, 733-737), a malaria vaccine should induce effective antibodies against this developmental stage. Evidence supporting the use of MSP-$1_{42}$ and MSP-$1_{19}$ in a malaria vaccine is extensive. MSP-$1_{19}$-specific mAbs inhibit *P. falciparum* growth in vitro (Blackman et al., 1990, supra) and passively protect mice against infection with *P. yoelii* (Majarian et al., 1984, J. Immunol. 132, 3131-3137; Ling et al., 1994, Parasite Immunol. 16, 63-67). Immunization of *Aotus* monkeys with native *P. falciparum* MSP-1 (Siddiqui, et al., 1987, Proc. Natl. Acad. Sci. USA 84, 3014-3018), or *S. cerevisiae* recombinant MSP-$1_{19}$ (Kumar et al., 1995, Mol. Med. 1, 325-332; Egan et al., 2000, Infect. Immun. 68, 1418-1427; Stowers et al. 2001, Trends Parasitol. 17, 415-419), protect against a homologous challenge. *E. coli*-expressed *P. yoelii* MSP-$1_{19}$ (Burns et al., 1989, J. Immunol. 143, 2670-2676) protects against a homologous challenge in rodent models. Antibodies raised against MSP-$1_{19}$ grown in yeast weakly inhibit *Plasmodium* growth in vitro (Gozalo et al., 1998, Am. J. Trop. Med. Hyg. 59, 991-997) however this antigen lacks correct structure and induces a strong allergic response (Keitel, W. A., 1999, Vaccine 18, 531-539). MSP-$1_{19}$ may not be an optimal vaccine because it does not induce strong T-helper cell responses (Quin et al., 2001, Eur. J. Immunol. 31, 72-81). Poor MSP-$1_{19}$ T-cell immunogenicity may be a consequence of its structural stability, which allows it to resist proteolysis, and therefore to resist processing and presentation to the immune system.

Thus, MSP-$1_{42}$ may be a better choice as a vaccine candidate (Quin and Langhorne, 2001, Infect. Immun. 69, 2245-2251). Immunization of *Aotus* monkeys with baculovirus-expressed recombinant MSP-$1_{42}$, protects against a homologous challenge and the anti-sera raised inhibit *P. falciparum* growth in vitro, but product yield is low and it is not yet available in clinical grade (Chang et al., 1996, Infect. Immun. 64, 253-261; Chang et al., 1992, J. Immunol. 149, 548-555). The monoclonal antibodies that inhibit *P. falciparum* growth in vitro also inhibit the secondary processing of MSP-$1_{42}$ to MSP-$1_{33}$ and MSP-$1_{19}$ and react with disulfide dependent conformational epitopes that are conserved among all known strains of *P. falciparum*, (Chappel and Holder, 1993, Mol. Biochem. Parasitol. 60, 103-111). MSP-$1_{19}$ as well as EGF Domain 2 affinity purified antibodies from immune human sera also prevent parasite invasion in vitro (Egan, et al, 1999, Parasite Immunol. 21, 133-139). Rabbit anti-sera raised against recombinant MSP-$1_{42}$ {Chang et al., 1992, supra) inhibit *P. falciparum* growth in vitro.

Vaccination of *Aotus nancymai* monkeys with molecules derived from either native full length MSP-1 (Siddiqui, 1977, Science, 197, 388-389) or C-terminal fragments of MSP-1 has shown protection against infection from a virulent FVO strain of P. falciparum (Chang et al., 1996, supra; Kumar et al., 2000, supra; Stowers, et al, 2001, Infect. Immun., 69, 1536-1546; Stowers, et al, 2002, PNAS, 99, 339-44). Other than the full length MSP-1, all the C-terminal MSP-1 fragments tested to date in Aotus monkeys were expressed from eukaryotic expression hosts. Expression in eukaryotic hosts can lead to post-translational modifications on MSP-1$_{42}$ such as N-glycosylation. Since P. falciparum does not normally N-glycosylate its proteins, this modification can lead to the addition of complex sugars that can alter protein conformation and thus alter immunogenicity (Stowers, 2002, supra). Within the native MSP-1$_{42}$ FVO sequence there are two predicted putative N-glycosylation sites.

Other attempts at producing MSP-1 in E. coli have not produced protective vaccines (Kumar, S. et al., 1995, Molecular Medicine 1, 325-332) due to problems with endotoxin contamination and possibly to an inability to establish correct disulfide bridging patterns. Therefore, not only is a good expression system needed for proper and sufficient expression of MSP-1$_{42}$ but also a good purification protocol is required which removes endotoxin contamination.

SUMMARY OF THE INVENTION

The present invention satisfies the needs discussed above. The present invention provides a vaccine grade E. coli expressed recombinant MSP-1$_{42}$ (FVO) that is properly folded. Characterization of the MSP-1$_{42}$ by immunoblotting with mAbs specific for conformation-dependent epitopes show that the protein contains properly formed epitopes on the highly structured MSP-1$_{19}$ portion. The purified protein was immunogenic in mice, rabbits and in Aotus monkeys. Rabbit anti-sera raised against the protein induced antibodies that inhibited P. falciparum growth in vitro. Aotus monkeys were protected against an experimental erythrocytic stage P. falciparum FVO strain challenge.

Therefore, a major aim of the present invention resides in the production of large amounts of MSP-1$_{42}$ that maintain conformational epitopes critical to epitope formation in pure form (>95% pure) for diagnostic, prophylactic and therapeutic purposes.

This may not seem complicated but, as with most strategies for protein purification, proved to be difficult and unpredictable. E. coli was chosen as a host, even though it had gone out of favor, for two reasons: (1) E. coli was known to produce high level of recombinant proteins and (2) recombinant proteins produced in E. coli are not glycosylated, which is consistent with the capabilities of malaria parasites. Several hurdles had to be overcome to achieve the desired expression level as soluble cytoplasmic form that can be sufficiently purified from host cell proteins without sacrificing proper folding of the protein. Problems with E. coli endotoxin levels and the presence of non-MSP-1$_{42}$ contaminants had to be resolved.

The P. falciparum FVO genomic DNA extending from amino acid 1349 to amino acid 1713 of the full length P. falciparum FVO MSP-1 (Miller, et al, 1993, Mol. Biochem. Parasitol., 59, 1-14) was amplified using primers containing restriction sites compatible with cloning into the expression construct pET(AT)PfMSP-1$_{42}$(3D7) (FIG. 1), which contains an MSP1$_{42}$ sequence from a P. falciparum 3D7 allele. The 3D7 allele was removed and the FVO allele was inserted into the expression vector using appropriate restriction sites. The sequenced clones were found to be identical in this region to Genbank Accession number, L20092. This construct was found to express inadequate amounts of the protein for use as a vaccine. In order to increase the expression of the protein, a single synonymous codon change at amino acid position #158, from ATC to ATA. (codon numbering starts from the ATG, initiation codon of the transcript) was introduced by PCR. The expressed protein is identical to the native amino acid for P. falciparum (FVO) MSP-1$_{42}$. The substitution was theorized to improve proper translation and folding of the protein, and hence its expression because it harmonized codon usage rates for this codon between E. coli and F. falciparum. Indeed, expression of the protein improved sufficiently to allow the use of the protein for a vaccine. The sequence of the final expressed FVO fragment is set forth in SEQ ID NO:1, with the sequence of the expressed protein in SEQ ID NO:2. Additional improvements to protein expression were achieved by further harmonizing codon frequencies between E. coli and P. falciparum. SEQ ID NO:3 sets forth the sequence of the FVO MSP1-42 gene with harmonized 5' 100 nucleotides, N-mod. SEQ ID NO:4 sets forth the complete MSP1$_{42}$ harmonized throughout the complete gene.

The E. coli expressed MSP-1$_{42}$ fragment is comprised from amino acid 1349 (Ala) to amino acid 1713 (Ser) from the full length P. falciparum FVO MSP-1 [Miller, 1993, supra]. The MSP-1$_{42}$ DNA used to prepare this clone was produced by PCR amplification of P. falciparum FVO genomic DNA; and the fragment was subcloned into the expression vector, pET(AT)PfMSP-1$_{42}$ (3D7), that was previously described for the expression of the MSP-1$_{42}$ 3D7 allele, (Angov et. al. (2003) Molec. Biochem. Parasitol; in press) (FIG. 1A). The final product contains 17 non-MSP-1$_{42}$ amino acids that include the hexa-histidine tag for Ni$^{+2}$ chelating chromatography at the N-terminus (FIG. 1B). Soluble expression of MSP-1$_{42}$ was induced by addition of 0.1 mM IPTG. MSP-1$_{42}$ was purified under GMP conditions using a two-step chromatographic method; that included a Ni$^{+2}$-NTA Sepharose affinity resin followed by a Q-Sepharose ion exchanger. The purified bulk was concentrated and buffer exchanged using ultrafiltration. The final protein was purified to greater than 95% of MSP-1. Vaccination of rabbits with the purified MSP-1$_{42}$ elicited neutralizing antibodies.

Therefore, it is an object of the present invention to provide a recombinant P. falciparum FVO MSP-1$_{42}$ for use in diagnostic assays and for production of antibodies.

It is another object of the present invention to provide compositions comprising purified recombinant P. falciparum FVO MSP-1$_{42}$.

It is yet another object of the present invention to provide novel vector constructs for recombinantly expressing P. falciparum MSP-1$_{42}$, as well as host cells transformed with said vector.

It is also an object of the present invention to provide a method for producing and purifying recombinant P. falciparum FVO MSP-1$_{42}$ protein comprising:

growing a host cell containing a vector expressing P. falciparum FVO MSP-1$_{42}$ proteins in a suitable culture medium, causing expression of said vector sequence as defined above under suitable conditions for production of soluble protein and, lysing said transformed host cells and recovering said MSP-1$_{42}$ protein such that it retains its native folding and is essentially free of host toxins.

It is also an object of the present invention to provide diagnostic and immunogenic uses of the recombinant P. falciparum FVO MSP-1$_{42}$ protein of the present invention, as well as to provide kits for diagnostic use for example in malaria screening and confirmatory antibody tests.

It is also an object of the present invention to provide monoclonal or polyclonal antibodies, more particularly human monoclonal antibodies or mouse monoclonal antibodies which are humanized which react specifically with MSP-$1_{42}$ epitopes, either comprised in peptides or conformational epitopes comprised in recombinant proteins.

It is also an object of the present invention to provide possible uses of anti-MSP-$1_{42}$ monoclonal antibodies for malaria antigen detection or for therapy of chronic malaria infection.

It is yet another object of the present invention to provide a malaria vaccine comprising MSP-$1_{42}$ of the present invention, in an amount effective to elicit an immune response in an animal against *P. falciparum*; and a pharmaceutically acceptable diluent, carrier, or excipient.

It is another object of the present invention to provide a method for eliciting in a subject an immune response against malaria, the method comprising administering to a subject a composition comprising MSP-$1_{42}$ of the present invention. In one aspect of the invention, the DNA vaccine is delivered along with an adjuvant, for example ADJUVANT B.

It is another object of the present invention to provide a method for preventing malaria infection in an animal comprising administering to the animal the MSP-$1_{42}$ of the present invention.

The vaccine according to the present invention is inherently safe, is not painful to administer, and should not result in adverse side effects to the vaccinated individual.

All the objects of the present invention are considered to have been met by the embodiments as set out below.

BRIEF DESCRIPTION OF THE DRAWINGS

FIG. 3: SDS-PAGE and immunoblotting of MSP-$1_{42}$ (FVO) GMP products. Electrophoreses were performed under non-reducing (Top Panel) and reducing (Bottom Panel) conditions. Samples in the top panel: Lane 1, Marker; lane 2, Purified bulk MSP-$1_{42}$ (FVO); lane 3, Formulated bulk MSP-$1_{42}$ (FVO) and lane 4, Final Container MSP-$1_{42}$ (FVO). Samples in the bottom panel: Lane 1, Marker; lane 2 Purified bulk MSP-$1_{42}$ (FVO) and lane 3, Final container MSP-$1_{42}$ (FVO).

FIGS. 4A and 4B: Course of daily parasitemia for individual monkeys. Monkeys were challenged on day 0 with 10,000 parasitized erythrocytes of *P. falciparum* FVO strain. Parasitemia was determined by counting erythrocytes on Giemsa-stained smears. A) shows the control group that was immunized with Pvs25 plus Freund's adjuvant. B) shows the experimental group that was immunized with MSP-$1_{42}$ and Freund's adjuvant.

FIG. 5: Western Blot Analysis of Secondary Processing Inhibition of Sera From *Aotus* Monkeys Sera from an *Aotus* monkey immunized with MSP1-42 (FVO)/Complete Freund's adjuvant was tested in a secondary-processing inhibition assay (PIA). This assay measures the ability of antibodies to inhibit the conversion of MSP1-42 (p42) to MSP1-33 (p33) and MSP1-19 (p19) from purified merozoites. The negative control for inhibition of secondary processing is incubation of merozoites with PMSF, this lane reveals weakly detectable levels of MSP1-33. The invasion inhibitory mAb 12.8, which inhibits parasite growth in vitro also, inhibits the secondary processing of p42 to p33. Pre-immune sera allows secondary processing to occur to form p33, while sera from day of challenge (DOC) and 6 weeks post challenge (DOC+6wk) inhibited the amount of the secondary processing to form p33.

DETAILED DESCRIPTION

Figure 1A:
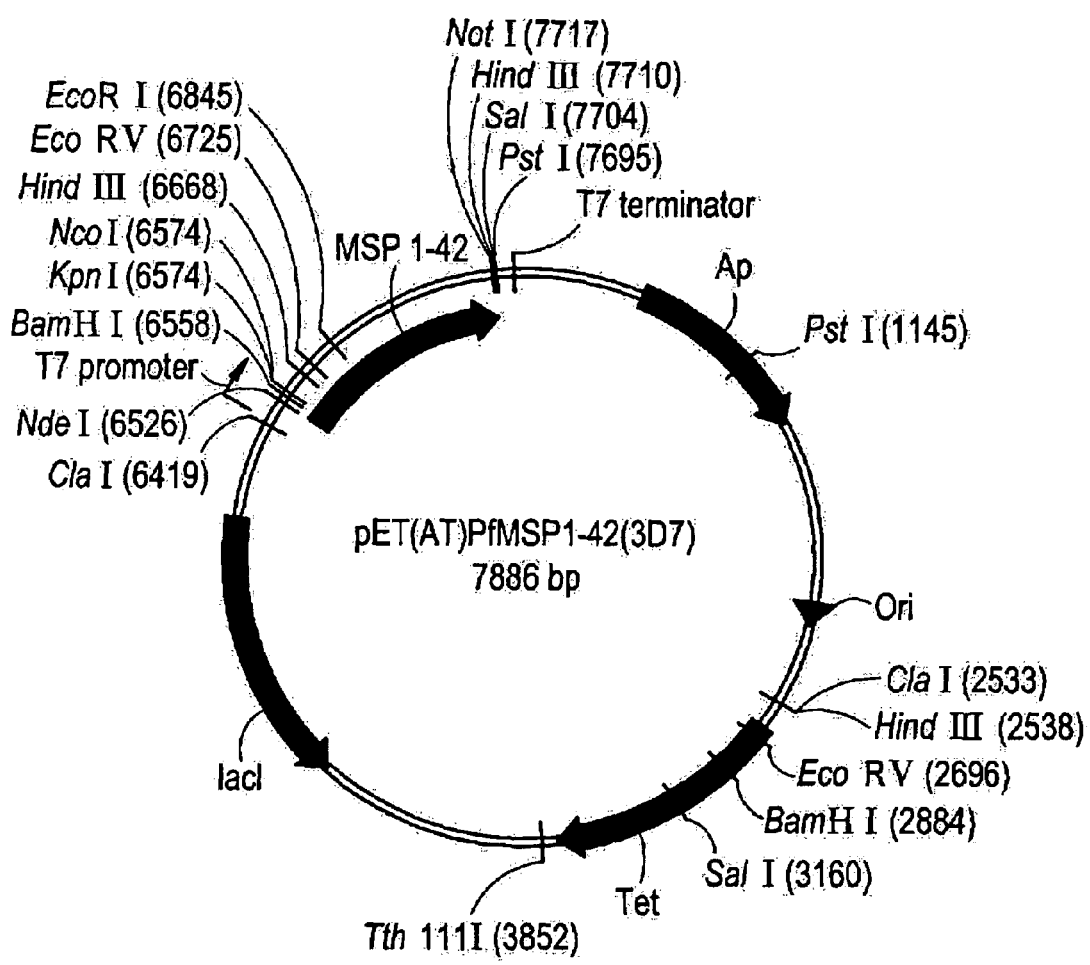
FIGS. 1A, 1B, 1C, 1D, and 1E. A) pET(AT)PfMSP-$1_{42}$ (3D7) Plasmid Map. B) PfMSP-$1_{42}$ (FVO) strain insert. C) pET(AT)FVO.A expression construct. D) pET(AT)FVO.B expression construct. E) pET(AT)FVO.C expression construct.

In the description that follows, a number of terms used in recombinant DNA, parasitology and immunology are extensively utilized. In order to provide a clearer and consistent understanding of the specification and claims, including the scope to be given such terms, the following definitions are provided.

In general, an 'epitope' is defined as a linear array of 3-10 amino acids aligned along the surface of a protein. In a linear epitope, the amino acids are joined sequentially and follow the primary structure of the protein. In a conformational epitope, residues are not joined sequentially, but lie linearly along the surface due to the conformation (folding) of the protein. With respect to conformational epitopes, the length of the epitope-defining sequence can be subject to wide variations. The portions of the primer structure of the antigen between the residues defining the epitope may not be critical to the structure of the conformational epitope. For example, deletion or substitution of these intervening sequences may not affect the conformational epitope provided sequences critical to epitope conformation are maintained (e.g. cysteines involved in disulfide bonding, glycosylation sites, etc.). A conformational epitope may also be formed by 2 or more essential regions of subunits of a homo-oligomer or hetero-oligomer. As used herein, 'epitope' or 'antigenic determinant' means an amino acid sequence that is immunoreactive. As used herein, an epitope of a designated polypeptide denotes epitopes with the same amino acid sequence as the epitope in the designated polypeptide, and immunologic equivalents thereof. Such equivalents also include strain, subtype (=genotype), or type (group)-specific variants, e.g. of the currently known sequences or strains belonging to *Plasmodium* such as 3D7, FVO and CAMP, or any other known or newly defined *Plasmodium* strain.

The term 'solid phase' intends a solid body to which the individual *P. falciparum* antigen is bound covalently or by noncovalent means such as hydrophobic, ionic, or van der Waals association.

The term 'biological sample' intends a fluid or tissue of a mammalian individual (e.g. an anthropoid, a human), reptilian, javian, or any other zoo or farm animal that commonly contains antibodies produced by the individual, more particularly antibodies against malaria. The fluid or tissue may also contain *P. falciparum* antigen. Such components are known in the art and include, without limitation, blood, plasma, serum, urine, spinal fluid, lymph fluid, secretions of the respiratory, intestinal or genitourinary tracts, tears, saliva, milk, white blood cells and myelomas. Body components include biological liquids. The term biological fluid refers to a fluid obtained from an organism. Some biological fluids are used as a source of other products, such as clotting factors (e.g. Factor VIII; C), serum albumin, growth hormone and the like.

The term 'immunologically reactive' means that the antigen in question will react specifically with anti-MSP-1 antibodies present in a body component from malaria infected individuals.

The term 'immune complex' intends the combination formed when an antibody binds to an epitope on an antigen.

The term 'MSP-1$_{42}$' as used herein refers to the polymorphic C-terminal 42 kDa protein fragment or polypeptide resulting from the processing by proteases of the 195 kDa membrane-anchored MSP-1 precursor. During merozoite invasion, the 42 kDa fragment is subjected to secondary processing producing a 33-kDa fragment (MSP-1$_{33}$) and a 19 kDa C-terminal fragment, (MSP-1$_{19}$) which remains attached via GPI to the surface of the invading merozoite. The MSP-1$_{42}$ protein extends from approximately amino acid (aa) 1349 to about aa 1713 of the full-length precursor protein (Genbank accession #L20092).

The term 'MSP-1$_{42}$' as used herein also includes analogs and truncated forms that are immunologically cross-reactive with natural MSP-1$_{42}$. By 'MSP-1$_{42}$' is intended MSP-1$_{42}$ from other strains of *Plasmodium falciparum*, or any other newly identified strain of *Plasmodium falciparum*.

The term 'homo-oligomer' as used herein refers to a complex of MSP-1$_{42}$ containing more than one MSP-1$_{42}$ monomer, e.g. MSP-1$_{42}$/MSP-1$_{42}$ dimers, trimers or tetramers, or any higher-order homo-oligomers of MSP-1$_{42}$ are all 'homo-oligomers' within the scope of this definition. The oligomers may contain one, two, or several different monomers of MSP-1$_{42}$ obtained from different strains of *Plasmodium falciparum* including for example 3D7, Camp, FVO, and others. Such mixed oligomers are still homo-oligomers within the scope of this invention, and may allow more universal diagnosis, prophylaxis or treatment of malaria.

The term 'purified' as applied to proteins herein refers to a composition wherein the desired protein comprises at least 35% of the total protein component in the composition. The desired protein preferably comprises at least 40%, more preferably at least about 50%, more preferably at least about 60%, still more preferably at least about 70%, even more preferably at least about 80%, even more preferably at least about 90%, and most preferably at least about 95% of the total protein component. The composition may contain other compounds such as carbohydrates, salts, lipids, solvents, and the like, without affecting the determination of the percentage purity as used herein. An 'isolated' MSP-1$_{42}$ protein intends a *Plasmodium* protein composition that is at least 35% pure.

The term 'essentially purified proteins' refers to proteins purified such that they can be used for in vitro diagnostic methods and as a prophylactic compound. These proteins are substantially free from cellular proteins, vector-derived proteins or other *Plasmodium* components. The proteins of the present invention are purified to homogeneity, at least 80% pure, preferably, 90%, more preferably 95%, more preferably 97%, more preferably 98%, more preferably 99%, even more preferably 99.5%.

The term 'recombinantly expressed' used within the context of the present invention refers to the fact that the proteins of the present invention are produced by recombinant expression methods be it in prokaryotes, or lower or higher eukaryotes as discussed in detail below.

The term 'lower eukaryote' refers to host cells such as yeast, fungi and the like. Lower eukaryotes are generally (but not necessarily) unicellular. Preferred lower eukaryotes are yeasts, particularly species within *Saccharomyces, Schizosaccharomyces, Kluveromyces, Pichia* (e.g. *Pichia pastoris*), *Hansenula* (e.g. *Hansenula polymorpha, Yarowia, Schwaniomyces, Schizosaccharomyces, Zygosaccharomyces* and the like. *Saccharomyces cerevisiae, S. carlsberoensis* and *K. lactis* are the most commonly used yeast hosts, and are convenient fungal hosts.

The term 'prokaryotes' refers to hosts such as *E. coli, Lactobacillus, Lactococcus, Salmonella, Streptococcus, Bacillus subtilis* or *Streptomyces*. Also these hosts are contemplated within the present invention.

The term 'higher eukaryote' refers to host cells derived from higher animals, such as mammals, reptiles, insects, and the like. Presently preferred higher eukaryote host cells are derived from Chinese hamster (e.g. CHO), monkey (e.g. COS and Vero cells), baby hamster kidney (BHK), pig kidney (PK15), rabbit kidney 13 cells (RK13), the human osteosarcoma cell line 143 B, the human cell line HeLa and human hepatoma cell lines like Hep G2, and insect cell lines (e.g. *Spodoptera frugiperda*). The host cells may be provided in suspension or flask cultures, tissue cultures, organ cultures and the like. Alternatively the host cells may also be transgenic animals.

The term 'polypeptide' refers to a polymer of amino acids and does not refer to a specific length of the product; thus, peptides, oligopeptides, and proteins are included within the definition of polypeptide. This term also does not refer to or exclude post-expression modifications of the polypeptide, for example, glycosylations, acetylations, phosphorylations and the like. Included within the definition are, for example, polypeptides containing one or more analogues of an amino acid (including, for example, unnatural amino acids, PNA, etc.), polypeptides with substituted linkages, as well as other modifications known in the art, both naturally occurring and non-naturally occurring.

The term 'recombinant polynucleotide or nucleic acid' intends a polynucleotide or nucleic acid of genomic, cDNA, semisynthetic, or synthetic origin which, by virtue of its origin or manipulation: (1) is not associated with all or a portion of a polynucleotide with which it is associated in nature, (2) is linked to a polynucleotide other than that to which it is linked in nature, or (3) does not occur in nature.

The term 'recombinant host cells', 'host cells', 'cells', 'cell lines', 'cell cultures', and other such terms denoting microorganisms or higher eukaryotic cell lines cultured as unicellular entities refer to cells which can be or have been, used as recipients for a recombinant vector or other transfer polynucleotide, and include the progeny of the original cell which has been transfected. It is understood that the progeny of a single parental cell may not necessarily be completely identical in morphology or in genomic or total DNA complement as the original parent, due to natural, accidental, or deliberate mutation.

The term 'replicon' is any genetic element, e.g., a plasmid, a chromosome, a virus, a cosmid, etc., that behaves as an autonomous unit of polynucleotide replication within a cell; i.e., capable of replication under its own control.

The term 'vector' is a replicon further comprising sequences providing replication and/or expression of a desired open reading frame.

The term 'control sequence' refers to polynucleotide sequences that are necessary to effect the expression of coding sequences to which they are ligated. The nature of such control sequences differs depending upon the host organism; in prokaryotes, such control sequences generally include promoter, ribosomal binding site, and terminators; in eukaryotes, generally, such control sequences include promoters, terminators and, in some instances, enhancers. The term 'control sequences' is intended to include, at a minimum, all components whose presence is necessary for expression, and may also include additional components, whose presence is advantageous, for example, leader sequences that govern secretion.

The term 'promoter' is a nucleotide sequence that is comprised of consensus sequences that allow the binding of RNA polymerase to the DNA template in a manner such that mRNA production initiates at the normal transcription initiation site for the adjacent structural gene.

The expression 'operably linked' refers to a juxtaposition wherein the components so described are in a relationship permitting them to function in their intended manner. A control sequence operably linked to a coding sequence is ligated in such a way that expression of the coding sequence is achieved under conditions compatible with the control sequences.

An 'open reading frame' (ORF) is a region of a polynucleotide sequence that encodes a polypeptide and does not contain stop codons; this region may represent a portion of a coding sequence or a total coding sequence.

A 'coding sequence' is a polynucleotide sequence that is transcribed into mRNA and/or translated into a polypeptide when placed under the control of appropriate regulatory sequences. The boundaries of the coding sequence are determined by a translation start codon at the 5'-terminus and a translation stop codon at the 3'-terminus. A coding sequence can include but is not limited to mRNA, DNA (including cDNA), and recombinant polynucleotide sequences.

The term 'immunogenic' refers to the ability of a substance to cause a humoral and/or cellular response, whether alone or when linked to a carrier, in the presence or absence of an adjuvant. 'Neutralization' refers to an immune response that blocks the infectivity, either partially or fully, of an infectious agent. A 'vaccine' is an immunogenic composition capable of eliciting protection against malaria, whether partial or complete. A vaccine may also be useful for treatment of an infected individual, in which case it is called a therapeutic vaccine.

The term. 'therapeutic' refers to a composition capable of treating malaria infection. The term 'effective amount' for a therapeutic or prophylactic treatment refers to an amount of epitope-bearing polypeptide sufficient to induce an immunogenic response in the individual to which it is administered, or to otherwise detectably immunoreact in its intended system (e.g., immunoassay). Preferably, the effective amount is sufficient to effect treatment, as defined above. The exact amount necessary will vary according to the application. For vaccine applications or for the generation of polyclonal antiserum/antibodies, for example, the effective amount may vary depending on the species, age, and general condition of the individual, the severity of the condition being treated, the particular polypeptide selected and its mode of administration, etc. It is also believed that effective amounts will be found within a relatively large, non-critical range. An appropriate effective amount can be readily determined using only routine experimentation. Preferred ranges of MSP-$1_{42}$ for prophylaxis of malaria disease are about 0.01 to 1000 ug/dose, more preferably about 0.1 to 100 ug/dose most preferably about 10-50 ug/dose. Several doses may be needed per individual in order to achieve a sufficient immune response and subsequent protection against malaria.

More particularly, the present invention contemplates essentially purified MSP-$1_{42}$ and a method for isolating or purifying recombinant MSP-$1_{42}$ protein.

The term 'MSP-$1_{42}$' refers to a polypeptide or an analogue thereof (e.g. mimotopes) comprising an amino acid sequence (and/or amino acid analogues) defining at least one MSP-$1_{42}$ epitope. Typically, the sequences defining the epitope correspond to the amino acid sequence of MSP-$1_{42}$ region of *P. falciparum* (either identically or via substitution of analogues of the native amino acid residue that do not destroy the epitope). The MSP-$1_{42}$ protein corresponds to a nucleotide sequence identified in SEQ ID NO:1, 3 or 4 and spans from amino acid 1349 to 1713 of MSP-1 FVO allele. Upon expression in the parasite system (non-glycosylated), it is believed to have an approximate molecular weight of 42 kDa as determined by SDS-PAGE. It is understood that these protein endpoints are approximations, e.g. the carboxy terminal end of MSP-$1_{42}$ could lie somewhere in the 1700 to 1720 amino acid region. The absolute C-terminus is not defined due to the post-translational modification that transfers MSP-1 to a GPI lipid membrane anchor.

The MSP-$1_{42}$ antigen used in the present invention is preferably a full-length protein, or a substantially full-length version, i.e. containing functional fragments thereof (e.g. fragments which are not missing sequence essential to the formation or retention of an epitope). Furthermore, the *P. falciparum* antigen of the present invention can also include other sequences that do not block or prevent the formation of the conformational epitope of interest. The presence or absence of a conformational epitope can be readily determined though screening the antigen of interest with an antibody as described in the Examples below (polyclonal serum or monoclonal to the conformational epitope) and comparing its reactivity to that of a denatured version of the antigen which retains only linear epitopes (if any).

The *P. falciparum* antigen of the present invention can be made by any recombinant method that provides the epitope of interest. For example, recombinant expression in *E. coli* is a preferred method to provide non-glycosylated antigens in 'native' conformation. This is most desirable because natural *P. falciparum* antigens are not glycosylated. Proteins secreted from mammalian cells may contain modifications including galactose or sialic acids that may be undesirable for certain diagnostic or vaccine applications. However, it may also be possible and sufficient for certain applications, as it is known for proteins, to express the antigen in other recombinant hosts such as baculovirus and yeast or higher eukaryotes, as long as glycosylation is inhibited.

The proteins according to the present invention may be secreted or expressed within compartments of the cell. Preferably, however, the proteins of the present invention are expressed within the cell and are released upon lysing the cells.

It is also understood that the isolates used in the examples section of the present invention were not intended to limit the scope of the invention and that an equivalent sequence from a *P. falciparum* isolate from another allele, e.g. 3D7, or CAMP, can be used to produce a recombinant MSP-$1_{42}$ protein using the methods described in the present application. Other new strains of *Plasmodium* may be a suitable source of MSP-$1_{42}$ sequence for the practice of the present invention.

The MSP-$1_{42}$ protein of the present invention is expressed as part of a recombinant vector. The present invention relates more particularly to the MSP-$1_{42}$ nucleic acid sequence in recombinant nucleic acid vector pET(AT)FVO as represented in SEQ ID NO:1, 3 or 4, or parts thereof. The MSP-$1_{42}$ (FVO) insert DNA was PCR amplified from *P. falciparum* (FVO) strain genomic DNA and ligated into the pET(AT)PfMSP-$1_{42}$ (3D7) (modified from vector pET32a from Novagen (Madison, Wis.)). This plasmid comprises, in sequence, a T7 promoter, optionally a lac operator, a ribosome-binding site, restriction sites to allow insertion of the structural gene and a T7 terminator sequence. Other vectors described include pET (K)FVO.B "initiation complex" (FIG. 1D) harmonized and pET(K)FVO.C [Full gene harmonized](FIG. 1E) wherein the ampicillin and tetracycline antibiotic resistance genes have been replaced with a kanamycin resistance gene. Examples of other plasmids which contain the T7 inducible promoter include the expression plasmids pET-17b, pET-11a, pET-24a-d(+), and pEt-9a, all from Novagen (Madison, Wis.); see the Novagen catalogue.

The present invention also contemplates host cells transformed with a recombinant vector as defined above. In a preferred embodiment, E. coli strain BL21(DE3) (F-ompT hsdSB(rB-mB-) gal dcm (DE3)) is employed. The above plasmids may be transformed into this strain or other strains of E. coli having the following characteristics: a T7 RNA polymerase gene, Lon, ompT protease mutants or any other E. coli with a protease deficiency such as E. coli B834 DE3, Origami DE3. Preferably, the host includes BL21 (DE3) and any of its precursors. Other host cells such as insect cells can be used taking into account that other cells may result in lower levels of expression.

Eukaryotic hosts include lower and higher eukaryotic hosts as described in the definitions section. Lower eukaryotic hosts include yeast cells well known in the art. Higher eukaryotic hosts mainly include mammalian cell lines known in the art and include many immortalized cell lines available from the ATCC, inluding HeLa cells, Chinese hamster ovary (CHO) cells, Baby hamster kidney (BHK) cells, PK15, RK13 and a number of other cell lines. MSP-$1_{42}$ expressed in these cells will be glycosylated unless the cells have been altered such that glycosylation of the recombinant protein is not possible. It is expected that when producing MSP-$1_{42}$ in a eukaryotic expression system, extensive investigation into methods for expressing, isolating, purifying, and characterizing the protein would be required as eukaryotic cells post-translationally modify this protein and this would alter protein structure and immunogenicity.

Methods for introducing vectors into cells are known in the art. Please see e.g., Maniatis, Fitsch and Sambrook, *Molecular Cloning; A Laboratory* Manual (1982) or *DNA Cloning*, Volumes I and II (D. N. Glover ed. 1985) for general cloning methods. Host cells provided by this invention include E. coli containing pET(AT)FVO.A [single pause site], E. coli containing pET(K)FVO.B [initiation complex harmonized] and E. coli containing pET(K)FVO.C[Full gene harmonized].

A preferred method for isolating or purifying MSP-$1_{42}$ as defined above is further characterized as comprising at least the following steps:

(i) growing a host cell as defined above transformed with a recombinant vector expressing MSP-$1_{42}$ proteins in a suitable culture medium, (ii) causing expression of said vector sequence as defined above under suitable conditions for production of a soluble protein, (iii) lysing said transformed host cells and recovering said MSP-$1_{42}$ protein such that it retains its native conformation and is essentially pure.

Once the host has been transformed with the vector, the transformed cells are grown in culture in the presence of the desired antibiotic. For FDA regulatory purposes, it is preferable to use tetracycline or kanamycin. When cells reach optimal biomass density, in this case about 0.4-0.6 OD$_{600}$ in small culture flasks or 5-7 OD$_{600}$ in bulk fermentors, the cells are induced to produce the recombinant protein. The inventors have found after trial and error that for expression of a soluble MSP-$1_{42}$, it was necessary to cool the culture to a range of about 10° C.-20° C., more preferably about 15° C.-28° C., most preferably about 24 to 26° C. prior to induction. The concentration of inducer, i.e. IPTG, added affects the maximal protein synthesis. It was found that a concentration of 0.1 mM IPTG was best, however, a range of 0.05 to 0.5 mM would be sufficient to produce 80-100% of maximal.

The cells were then collected and lysed to release the recombinant protein. Preferably, lysis should occur at a paste to buffer ratio of 1:3 w/v to reduce viscosity and volume of sample loaded on Ni-NTA column. Preferably, lysis is in the presence of imidazole that reduces non-specific binding of E. coli proteins to Ni resin, and benzonase that is able to digest E. coli nucleic acids. Lysis is preferably at a temperature of about 0° C.-24° C., more preferably about 5-15° C. in order to retain native folding of the MSP-$1_{42}$ protein and to reduce proteolysis. A high salt concentration of about 0.5-1.0 M is preferable during extraction procedures. Salts used include NaCl or other monovalent ions.

Preferably, the E. coli endotoxin is separated and removed from the recombinant protein. This can be done several ways. For MSP-$1_{42}$, endotoxin was removed by applying to a Ni$^{+2}$-NTA column. The removal of endotoxin depended on washing in high salt, about 0.5 to about 1.5 M, preferably about 1000 mM NaCl at a flow rate of about 20 to about 35 ml/min, preferably about 30 ml/min. The cell paste to resin ratio can be about 5:1 to about 20:1 w/v, preferably about 12:1 w/v. The recombinant protein can be eluted by addition of high concentration of imidazole, 500 to 1500 mM, preferably 1000 mM at pH 8.0, in a phosphate buffer of about 5-25 mM, more preferably about 10 mM sodium phosphate buffer.

At this point the recombinant protein is about 50% pure. If further purity is required, ion-exchange chromatography can be utilized. The column is preferably with an ionic character such that a pH to enhance protein binding. Reducing the buffer pH to 7.2 and increasing the salt to 250 mM elutes the protein from the resin. Under these conditions, the endotoxin and nucleic acid remain bound to the resin and are therefore removed from the protein.

The present invention further relates to a composition comprising at least one of the following:

MSP-$1_{42}$ alone (SEQ ID NO: 1, 3, and 4) spanning amino acids to 1349-1713 of MSP-1, MSP-$1_{42}$ plus 17 amino acids at N-terminal in final expression vector construct pET(AT)FVO.A, the final expressed product referred to as FMP003. The peptide sequence contains additional nonMSP1 amino acids, i.e. MAHHHHHH-PGGSGSGTM (SEQ ID NO:6 containing His6Tag and non-MSP1 nucleotide linker sequence.

The present invention also relates to a composition-comprising peptides or polypeptides as described above, for in vitro detection of malaria antibodies present in a biological sample.

The present invention also relates to a composition comprising at least one of the following MSP-$1_{42}$ conformational epitopes:

epitope recognized by monoclonal antibodies 12.10, 12.8, 7.5, 2.2, 1E1 (Blackman et al., 1990, supra; Conway et al., 1991, Parasitology 103, 1-6; McBride et al., 1982, Science 217, 254-257; Mackay et al., 1985, Embo J. 4, 3823-3829).

epitope recognized by monoclonal antibody 5.2 (Chang et al., 1988, Exp. Parasitol. 67, 1-11).

The present invention also relates to an MSP-$1_{42}$ specific antibody raised upon immunizing an animal with a peptide or protein composition, with said antibody being specifically reactive with any of the polypeptides or peptides as defined above, and with said antibody being preferably a monoclonal antibody.

The present invention also relates to an MSP-$1_{42}$ specific antibody screened from a variable chain library in plasmids or phages or from a population of human B-cells by means of a process known in the art, with said antibody being reactive with any of the polypeptides or peptides as defined above, and with said antibody being preferably a monoclonal antibody.

The MSP-1$_{42}$ specific monoclonal antibodies of the invention can be produced by any hybridoma liable to be formed according to classical methods from splenic or lymph node cells of an animal, particularly from a mouse or rat, immunized against the *Plasmodium* polypeptides or peptides according to the invention, as defined above on the one hand, and of cells of a myeloma cell line on the other hand, and to be selected by the ability of the hybridoma to produce the monoclonal antibodies recognizing the polypeptides which has been initially used for the immunization of the animals.

The antibodies involved in the invention can be labelled by an appropriate label of the enzymatic, fluorescent, or radioactive type.

The monoclonal antibodies according to this preferred embodiment of the invention may be humanized versions of mouse monoclonal antibodies made by means of recombinant DNA technology, departing from parts of mouse and/or human genomic DNA sequences coding for H and L chains from cDNA or genomic clones coding for H and L chains.

Alternatively the monoclonal antibodies according to this preferred embodiment of the invention may be human monoclonal antibodies. These antibodies according to the present embodiment of the invention can also be derived from human peripheral blood lymphocytes of patients infected with malaria, or vaccinated against malaria. Such human monoclonal antibodies are prepared, for instance, by means of human peripheral blood lymphocytes (PBL) repopulation of severe combined immune deficiency (SCID) mice, or by means of transgenic mice in which human immunoglobulin genes have been used to replace the mouse genes.

The invention also relates to the use of the proteins or peptides of the invention, for the selection of recombinant antibodies by the process of repertoire cloning.

Antibodies directed to peptides or single or specific proteins derived from a certain strain may be used as a medicament, more particularly for incorporation into an immunoassay for the detection of *Plasmodium* strains for detecting the presence of MSP-1$_{42}$ antigens, or antigens containing MSP-1$_{42}$ epitopes, for prognosing/monitoring of malaria disease, or as therapeutic agents.

Alternatively, the present invention also relates to the use of ant of the above-specified MSP-1$_{42}$ monoclonal antibodies for the preparation of an immunoassay kit for detecting the presence of MSP-1$_{42}$ antigen or antigens containing MSP-1$_{42}$ epitopes in a biological sample, for the preparation of a kit for prognosing/monitoring of malaria disease or for the preparation of a malaria medicament.

The present invention also relates to a method for in vitro diagnosis or detection of malaria antigen present in a biological sample, comprising at least the following steps:

(i) contacting said biological sample with any of the MSP-1$_{42}$ specific monoclonal antibodies as defined above, preferably in an immobilized form under appropriate conditions which allow the formation of an immune complex, (ii) removing unbound components, (iii) incubating the immune complexes formed with heterologous antibodies, which specifically bind to the antibodies present in the sample to be analyzed, with said heterologous antibodies conjugated to a detectable label under appropriate conditions, (iv) detecting the presence of said immune complexes visually or mechanically (e.g. by means of densitometry, fluorimetry, colorimetry).

The present invention also relates to a kit for in vitro diagnosis of a malaria antigen present in a biological sample, comprising:

at least one monoclonal antibody as defined above, with said antibody being preferentially immobilized on a solid substrate, a buffer or components necessary for producing the buffer enabling binding reaction between these antibodies and the malaria antigens present in the biological sample, and a means for detecting the immune complexes formed in the preceding binding reaction.

The kit can possibly also include an automated scanning and interpretation device for inferring the malaria antigens present in the sample from the observed binding pattern.

Monoclonal antibodies according to the present invention are suitable both as therapeutic and prophylactic agents for treating or preventing malaria infection in susceptible malaria-infected subjects. Subjects include rodents such as mice or guinea pigs, monkeys, and other mammals, including humans.

In general, this will comprise administering a therapeutically or prophylactically effective amount of one or more monoclonal antibodies of the present invention to a susceptible subject or one exhibiting malaria infection. Any active form of the antibody can be administered, including Fab and F(ab')$_2$ fragments. Antibodies of the present invention can be produced in any system, including insect cells, baculovirus expression systems, chickens, rabbits, goats, cows, or plants such as tomato, potato, banana or strawberry. Methods for the production of antibodies in these systems are known to a person with ordinary skill in the art. Preferably, the antibodies used are compatible with the recipient species such that the immune response to the MAbs does not result in clearance of the MAbs before parasite can be controlled, and the induced immune response to the MAbs in the subject does not induce "serum sickness" in the subject. Preferably, the MAbs administered exhibit some secondary functions such as binding to Fc receptors of the subject.

Treatment of individuals having malaria infection may comprise the administration of a therapeutically effective amount of MSP-1$_{42}$ antibodies of the present invention. The antibodies can be provided in a kit as described below. The antibodies can be used or administered as a mixture, for example in equal amounts, or individually, provided in sequence, or administered all at once. In providing a patient with antibodies, or fragments thereof, capable of binding to MSP-1$_{42}$, or an antibody capable of protecting against malaria in a recipient patient, the dosage of administered agent will vary depending upon such factors as the patient's age, weight, height, sex, general medical condition, previous medical history, etc.

In general, it is desirable to provide the recipient with a dosage of antibody which is in the range of from about 1 pg/kg-100 pg/kg, 100 pg/kg-500 pg/kg, 500 pg/kg-1 ng/kg, 1 ng/kg-100 ng/kg, 100 ng/kg-500 ng/kg, 500 ng/kg-1 ug/kg, 1 ug/kg-100 ug/kg, 100 ug/kg-500 ug/kg, 500 ug/kg-1 mg/kg, 1 mg/kg-50 mg/kg, 50 mg/kg-100 mg/kg, 100 mg/kg-500 mg/kg, 500 mg/kg-1 g/kg, 1 g/kg-5 g/kg, 5 g/kg-10 g/kg (body weight of recipient), although a lower or higher dosage may be administered.

In a similar approach, another prophylactic use of the monoclonal antibodies of the present invention is the active immunization of a patient using an anti-idiotypic antibody raised against one of the present monoclonal antibodies. Immunization with an anti-idiotype that mimics the structure of the epitope could elicit an active anti-MSP-1$_{42}$ response (Linthicum, D. E. and Farid, N. R., Anti-Idiotypes, Receptors, and Molecular Mimicry (1988), pp 1-5 and 285-300).

Likewise, active immunization can be induced by administering one or more antigenic and/or immunogenic epitopes as a component of a subunit vaccine. Vaccination could be performed orally or parenterally in amounts sufficient to enable the recipient to generate protective antibodies against this biologically functional region, prophylactically or therapeutically. The host can be actively immunized with the antigenic/immunogenic peptide in pure form, a fragment of the peptide, or a modified form of the peptide. One or more amino acids, not corresponding to the original protein sequence can be added to the amino or carboxyl terminus of the original peptide, or truncated form of peptide. Such extra amino acids are useful for coupling the peptide to another peptide, to a large carrier protein, or to a support. Amino acids that are useful for these purposes include: tyrosine, lysine, glutamic acid, aspartic acid, cysteine and derivatives thereof. Alternative protein modification techniques may be used e.g., $NH_2$-acetylation or COOH-terminal amidation, to provide additional means for coupling or fusing the peptide to another protein or peptide molecule or to a support.

The antibodies capable of protecting against malaria are intended to be provided to recipient subjects in an amount sufficient to effect a reduction in the malaria infection symptoms. An amount is said to be sufficient to "effect" the reduction of infection symptoms if the dosage, route of administration, etc. of the agent are sufficient to influence such a response. Responses to antibody administration can be measured by analysis of subject's vital signs.

The present invention more particularly relates to a composition comprising at least one of the above-specified peptides or a recombinant MSP-$1_{42}$ protein composition as defined above, for use as a vaccine for immunizing a mammal, preferably humans, against malaria, comprising administering a sufficient amount of the composition possibly accompanied by pharmaceutically acceptable adjuvant(s), to produce an immune response.

Immunogenic compositions can be prepared according to methods known in the art. The present compositions comprise an immunogenic amount of one or more recombinant MSP-$1_{42}$ protein or peptides as defined above, usually combined with a pharmaceutically acceptable carrier, preferably further comprising an adjuvant.

The proteins of the present invention, preferably purified MSP-$1_{42}$ from one of *P. falciparum*, e.g. FVO and 3D7, are expected to provide a particularly useful vaccine antigen, since the antigen is able to induce invasion inhibitory antibodies as well as high titer antibodies that react with schizont-infected-erythrocytes.

Pharmaceutically acceptable carriers include any carrier that does not itself induce the production of antibodies harmful to the individual receiving the composition. Suitable carriers are typically large, slowly metabolized macromolecules such as proteins, polysaccharides, polylactic acids, polyglycolic acids, polymeric amino acids, amino acid copolymers; and inactive virus particles. Such carriers are well known to those of ordinary skill in the art.

Preferred adjuvants to enhance effectiveness of the composition include, but are not limited to: montanide, aluminum hydroxide (alum), N-acetyl-muramyl-L-threonyl-D-isoglutamine (thr-MDP) as found in U.S. Pat. No. 4,606,918, N-acetyl-normuramyl-L-alanyl-D-isoglutamine(nor-MDP), N-acetylmuramyl-L-alanyl-D-isoglutaminyl-L-alanine-2-(1'-2'-dipalmitoyl-sn-glycero-3-hydroxyphosphoryloxy)-ethylamine (MTP-PE) and RIBI, which contains three components extracted from bacteria, monophosphoryl lipid A, trehalose dimycolate, and cell wall skeleton (MPL+TDM+CWS) in a 2% squalene/Tween 80 emulsion. Any of the 3 components MPL, TDM or CWS may also be used alone or combined 2 by 2. Additionally, adjuvants such as Stimulon (Cambridge Bioscience, Worcester, Mass.) or SAF-1 (Syntex) may be used. Further, Complete Freund's Adjuvant (CFA) and Incomplete Freund's Adjuvant (IFA) may be used for non-human applications and research purposes.

The adjuvant used in the examples below, Adjuvant B, is described in U.S. Pat. No. 6,146,632, with the formulation 10.68 mg squalene, 11.86 mg tocopherol, 4.85 mg Tween 80, 50 ug 3D-MPL, and 50 ug QS21 and consisting of an oil-in water emulsion comprising the squalene and alpha-tocopherol, the emulsion being in admixture with the QS21 and 3-DPML;

All documents cited herein are hereby incorporated by reference thereto.

The immunogenic compositions typically will contain pharmaceutically acceptable vehicles, such as water, saline, glycerol, ethanol, etc. Additionally, auxiliary substances, such as wetting or emulsifying agents, pH buffering substances, preservatives, and the like, may be included in such vehicles.

Typically, the immunogenic compositions are prepared as injectables, either as liquid solutions or suspensions; solid forms suitable for solution in, or suspension in, liquid vehicles prior to injection may also be prepared. The preparation also may be emulsified or encapsulated in liposomes for enhanced adjuvant effect. The MSP-$1_{42}$ proteins of the invention may also be incorporated into Immune Stimulating Complexes together with saponins, for example QuilA (IS-COMS).

Immunogenic compositions used as vaccines comprise a 'sufficient amount' or 'an immunologically effective amount' of the proteins of the present invention, as well as any other of the above-mentioned components, as needed. 'Immunologically effective amount', means that the administration of that amount to an individual, either in a single dose or as part of a series, is effective for treatment, as defined above. This amount varies depending upon the health and physical condition of the individual to be treated, the taxonomic group of individual to be treated (e.g. nonhuman primate, primate, etc.), the capacity of the individual's immune system to synthesize antibodies, the degree of protection desired, the formulation of the vaccine, the treating doctor's assessment of the medical situation, the strain of malaria infection, and other relevant factors. It is expected that the amount will fall in a relatively broad range that can be determined through routine trials. Usually, the amount will vary from 0.01 to 1000 ug/dose, more particularly from about 1.0 to 100 ug/dose most preferably from about 10 to 50 ug/dose.

The proteins may also serve as vaccine carriers to present homologous (e.g. other malaria antigens, such as EBA-175 or AMA-1) or heterologous (non-malaria) antigens. In this use, the proteins of the invention provide an immunogenic carrier capable of stimulating an immune response to other antigens. The antigen may be conjugated either by conventional chemical methods, or may be cloned into the gene encoding MSP-$1_{42}$ fused to the 5' end or the 3' end of the MSP-$1_{42}$ gene. The vaccine may be administered in conjunction with other immunoregulatory agents.

The compounds of the present invention can be formulated according to known methods to prepare pharmaceutically useful compositions, whereby these materials, or their functional derivatives, are combined in admixture with a pharmaceutically acceptable carrier vehicle. Suitable vehicles and their formulation, inclusive of other human proteins, e.g., human serum albumin, are described, for example, in *Remington's Pharmaceutical Sciences* (16th ed., Osol, A. ed., Mack Easton Pa. (1980)). In order to form a pharmaceutically acceptable composition suitable for effective administration, such compositions will contain an effective amount of the above-described compounds together with a suitable amount of carrier vehicle.

Additional pharmaceutical methods may be employed to control the duration of action. Control release preparations may be achieved through the use of polymers to complex or absorb the compounds. The controlled delivery may be exercised by selecting appropriate macromolecules (for example polyesters, polyamino acids, polyvinyl, pyrrolidone, ethylenevinylacetate, methylcellulose, carboxymethylcellulose, or protamine sulfate) and the concentration of macromolecules as well as the method of incorporation in order to control release. Another possible method to control the duration of action by controlled release preparations is to incorporate the compounds of the present invention into particles of a polymeric material such as polyesters, polyamino acids, hydrogels, poly(lactic acid) or ethylene vinylacetate copolymers. Alternatively, instead of incorporating these agents into polymeric particles, it is possible to entrap these materials in microcapsules prepared, for example, interfacial polymerization, for example, hydroxymethylcellulose or gelatin-microcapsules and poly(methylmethacylate)-microcapsules, respectively, or in colloidal drug delivery systems, for example, liposomes, albumin microspheres, microemulsions, nanoparticles, and nanocapsules or in macroemulsions. Such techniques are disclosed in *Remington's Pharmaceutical Sciences* (1980).

Administration of the compounds, whether antibodies or vaccines, disclosed herein may be carried out by any suitable means, including parenteral injection (such as intraperitoneal, subcutaneous, or intramuscular injection), in ovo injection of birds, orally, or by topical application of the antibodies (typically carried in a pharmaceutical formulation) to an airway surface. Topical application of the antibodies to an airway surface can be carried out by intranasal administration (e.g., by use of dropper, swab, or inhaler which deposits a pharmaceutical formulation intranasally). Topical application of the antibodies to an airway surface can also be carried out by inhalation administration, such as by creating respirable particles of a pharmaceutical formulation (including both solid particles and liquid particles) containing the antibodies as an aerosol suspension, and then causing the subject to inhale the respirable particles. Methods and apparatus for administering respirable particles of pharmaceutical formulations are well known, and any conventional technique can be employed. Oral administration may be in the form of an ingestable liquid or solid formulation.

The treatment may be given in a single dose schedule, or preferably a multiple dose schedule in which a primary course of treatment may be with 1-10 separate doses, followed by other doses given at subsequent time intervals required to maintain and or reinforce the response, for example, at 1-4 months for a second dose, and if needed, a subsequent dose(s) after several months. Examples of suitable treatment schedules include: (i) 0, 1 month and 6 months, (ii) 0, 7 days and 1 month, (iii) 0 and 1 month, (iv) 0 and 6 months, or other schedules sufficient to elicit the desired responses expected to reduce disease symptoms, or reduce severity of disease.

The present invention also provides kits that are useful for carrying out the present invention. The present kits comprise a first container means containing the above-described antibodies. The kit also comprises other container means containing solutions necessary or convenient for carrying out the invention. The container means can be made of glass, plastic or foil and can be a vial, bottle, pouch, tube, bag, etc. The kit may also contain written information, such as procedures for carrying out the present invention or analytical information, such as the amount of reagent contained in the first container means. The container means may be in another container means, e.g. a box or a bag, along with the written information.

The present invention also relates to a method for in vitro diagnosis of malaria antibodies present in a biological sample, comprising at least the following steps (i) contacting said biological-sample with a composition comprising any of the MSP-1$_{42}$ peptides as defined above, preferably in an immobilized form under appropriate conditions which allow the formation of an immune complex, wherein said peptide or protein can be a biotinylated peptide or protein which is covalently bound to a solid substrate by means of streptavidin or avidin complexes, (ii) removing unbound components, (iii) incubating the immune complexes formed with heterologous antibodies, with said heterologous antibodies having conjugated to a detectable label under appropriate conditions, (iv) detecting the presence of said immune complexes visually or mechanically (e.g. by means of densitometry, fluorimetry, colorimetry).

The present invention also relates to a kit for determining the presence of malaria antibodies, in a biological sample, comprising:

at least one peptide or protein composition as defined above, possibly in combination with other polypeptides or peptides from *Plasmodium* or other types of malaria parasite, with said peptides or proteins being preferentially immobilized on a solid support, more preferably on different microwells of the same ELISA plate, and even more preferentially on one and the same membrane strip, a buffer or components necessary for producing the buffer enabling binding reaction between these polypeptides or peptides and the antibodies against malaria present in the biological sample, means for detecting the immune complexes formed in the preceding binding reaction, possibly also including an automated scanning and interpretation device for inferring the malaria parasite present in the sample from the observed binding pattern.

The immunoassay methods according to the present invention utilize MSP-1$_{42}$ domains that maintain linear (in case of peptides) and conformational epitopes (proteins) recognized by antibodies in the sera from individuals infected with a malaria parasite. The MSP-1$_{42}$ antigens of the present invention may be employed in virtually any assay format that employs a known antigen to detect antibodies. A common feature of all of these assays is that the antigen is contacted with the body component suspected of containing malaria antibodies under conditions that permit the antigen to bind to any such antibody present in the component. Such conditions will typically be physiologic temperature, pH and ionic strength using an excess of antigen. The incubation of the antigen with the specimen is followed by detection of immune complexes comprised of the antigen.

Design of the immunoassays is subject to a great deal of variation, and many formats are known in the art. Protocols may, for example, use solid supports, or immunoprecipitation. Most assays involve the use of labeled antibody or polypeptide; the labels may be, for example, enzymatic, fluorescent, chemiluminescent, radioactive, or dye molecules. Assays which amplify the signals from the immune complex are also known; examples of which are assays which utilize biotin and avidin or streptavidin, and enzyme-labeled and mediated immunoassays, such as ELISA assays.

The immunoassay may be, without limitation, in a heterogeneous or in a homogeneous format, and of a standard or competitive type. In a heterogeneous format, the polypeptide is typically bound to a solid matrix or support to facilitate separation of the sample from the polypeptide after incubation. Examples of solid supports that can be used are nitrocellulose (e.g., in membrane or microtiter well form), polyvinyl chloride (e.g., in sheets or microtiter wells), polystyrene latex (e.g., in beads or microtiter plates, polyvinylidine fluoride (known as Immunolon.™.), diazotized paper, nylon membranes, activated beads, and Protein A beads. For example, Dynatech Immunolon.™.1 or Immunlon.™. 2 microtiter plates or 0.25 inch polystyrene beads (Precision Plastic Ball) can be used in the heterogeneous format. The solid support containing the antigenic polypeptides is typically washed after separating it from the test sample, and prior to detection of bound antibodies. Both standard and competitive formats are known in the art.

In a homogeneous format, the test sample is incubated with the combination of antigens in solution. For example, it may be under conditions that will precipitate any antigen-antibody complexes that are formed. Both standard and competitive formats for these assays are known in the art.

In a standard format, the amount of malaria antibodies in the antibody-antigen complexes is directly monitored. This may be accomplished by determining whether labeled anti-xenogeneic (e.g. anti-human) antibodies which recognize an epitope on anti-malaria antibodies will bind due to complex formation. In a competitive format, the amount of malaria antibodies in the sample is deduced by monitoring the competitive effect on the binding of a known amount of labeled-antibody (or other competing ligand) in the complex.

Complexes formed comprising anti-malaria antibody (or in the case of competitive assays, the amount of competing antibody) are detected by any of a number of known techniques, depending on the format. For example, unlabeled malaria antibodies in the complex may be detected using a conjugate of anti-xenogeneic Ig complexed with a label (e.g. an enzyme label).

In an immunoprecipitation or agglutination assay format the reaction between the malaria antigens and the antibody forms a network that precipitates from the solution or suspension and forms a visible layer or film of precipitate. If no anti-malaria antibody is present in the test specimen, no visible precipitate is formed.

There currently exist three specific types of particle agglutination (PA) assays. These assays are used for the detection of antibodies to various antigens when coated to a support. One type of this assay is the hemagglutination assay using red blood cells (RBCs) that are sensitized by passively adsorbing antigen (or antibody) to the RBC. The addition of specific antigen antibodies present in the body component, if any, causes the RBCs coated with the purified antigen to agglutinate.

To eliminate potential non-specific reactions in the hemagglutination assay, two artificial carriers may be used instead of RBC in the PA. The most common of these are latex particles. However, gelatin particles may also be used. The assays utilizing either of these carriers are based on passive agglutination of the particles coated with purified antigens.

The MSP-1$_{42}$ proteins, peptides, or antigens of the present invention will typically be packaged in the form of a kit for use in these immunoassays. The kit will normally contain in separate containers the MSP-1$_{42}$ antigen, control antibody formulations (positive and/or negative), labeled antibody when the assay format requires the same and signal generating reagents (e.g. enzyme substrate) if the label does not generate a signal directly. The MSP-1$_{42}$ antigen may be already bound to a solid matrix or separate with reagents for binding it to the matrix. Instructions (e.g. written, tape, CD-ROM, etc.) for carrying out the assay usually will be included in the kit.

Immunoassays that utilize the MSP-1$_{42}$ antigen are useful in screening blood for the preparation of a supply from which potentially infective malaria parasite is lacking. The method for the preparation of the blood supply comprises the following steps. Reacting a body component, preferably blood or a blood component, from the individual donating blood with MSP-1$_{42}$ proteins of the present invention to allow an immunological reaction between malaria antibodies, if any, and the MSP-1$_{42}$ antigen. Detecting whether anti-malaria antibody— MSP-1$_{42}$ antigen complexes are formed as a result of the reacting. Blood contributed to the blood supply is from donors that do not exhibit antibodies to the native MSP-1 antigens.

The present invention further contemplates the use of MSP-1$_{42}$ proteins, or parts thereof as defined above, for in vitro monitoring malaria infection or prognosing the response to treatment (for instance with chloroquine, mefloquine, Malarone) of patients suffering from malaria infection comprising:

incubating a biological sample from a patient with malaria infection with an MSP-1$_{42}$ protein or a suitable part thereof under conditions allowing the formation of an immunological complex, removing unbound components, calculating the anti-MSP-1$_{42}$ titers present in said sample (for example at the start of and/or during the course of therapy), monitoring the natural course of malaria infection, or prognosing the response to treatment of said patient on the basis of the amount anti-MSP-1$_{42}$ titers found in said sample at the start of treatment and/or during the course of treatment.

Patients who show a decrease of 2, 3, 4, 5, 7, 10, 15, or preferably more than 20 times of the initial anti-MSP-1$_{42}$ titers could be concluded to be long-term, sustained responders to malaria therapy.

It is to be understood that smaller fragments of the above-mentioned peptides also fall within the scope of the present invention. Said smaller fragments can be easily prepared by chemical synthesis and can be tested for their ability to be used in an assay as detailed above.

The present invention also relates to a kit for monitoring malaria infection or prognosing the response to treatment (for instance to medication) of patients suffering from malaria infection comprising:

at least one MSP-1$_{42}$ peptide as defined above, a buffer or components necessary for producing the buffer enabling the binding reaction between these proteins or peptides and the anti-MSP-1$_{42}$ antibodies present in a biological sample, means for detecting the immune complexes formed in the preceding binding reaction, possibly also an automated scanning and interpretation device for inferring a decrease of anti-MSP-1$_{42}$ titers during the progression of treatment.

The present invention also relates to a serotyping assay for detecting one or more serological types or alleles of malaria parasite present in a biological sample, more particularly for detecting antibodies of the different types or alleles of malaria parasites to be detected combined in one assay format, comprising at least the following steps:

(i) contacting the biological sample to be analyzed for the presence of malaria antibodies of one or more serological types, with at least one of the MSP-1$_{42}$ compositions as defined above, preferentially in an immobilized form under appropriate conditions which allow the formation of an immune complex, (ii) removing unbound components, (iii) incubating the immune complexes formed with heterologous antibodies, with said heterologous antibodies-being conjugated to a detectable label under appropriate conditions, (iv) detecting the presence of said immune complexes visually or mechanically (e.g. by means of densitometry, fluorometry, calorimetry) and inferring the presence of one or more malaria serological types present from the observed binding pattern.

It is to be understood that the compositions of proteins or peptides used in this method are recombinantly expressed type-specific or allele-specific proteins or type-specific peptides.

The present invention further relates to a kit for serotyping one or more serological types or alleles of malaria parasite present in a biological sample, more particularly for detecting the antibodies to these serological types of malaria parasites comprising:

at least one MSP-$1_{42}$ protein or MSP-$1_{42}$ peptide, as defined above, a buffer or components necessary for producing the buffer enabling the binding reaction between these proteins or peptides and the anti-MSP-1 antibodies present in a biological sample, means for detecting the immune complexes formed in the preceding binding reaction, possibly also an automated scanning and interpretation device for detecting the presence of one or more serological types present from the observed binding pattern.

The present invention also relates to the use of a peptide or protein composition as defined above, for immobilization on a solid support and incorporation into a reversed phase hybridization assay, preferably for immobilization as parallel lines onto a solid support such as a membrane strip, for determining the presence or the genotype of malaria parasite according to a method as defined above. Combination with other type-specific or allele-specific antigens from other malaria parasites also lies within the scope of the present invention.

The contents of all cited references (including literature references, issued patents, published patent applications, and co-pending patent applications) cited throughout this application are hereby expressly incorporated by reference.

Other features of the invention will become apparent in the course of the following descriptions of exemplary embodiments that are given for illustration of the invention and are not intended to be limiting thereof.

The following MATERIALS AND METHODS were used in the examples that follow.

Construction of Expression Vector pET(AT)FVO.A.

Molecular cloning and bacterial transformations were performed as follows: MSP-$1_{42}$ fragment of FVO strain DNA was amplified by PCR from *P. falciparum* FVO genomic DNA by using the primers FVO-PCR1; 5'-GGGTCGGTACCATGGCAGTAACTCCTTCCGTAATTGAT-3' (SEQ ID NO:7) and FVO-PCR2, 5'GGATCAGATGCGGCCGCTTAACTGCAGAAAATACCATCGAAAAGTGGA-3' (SEQ ID NO:8). The primers contained restriction sites for restriction endonucleases, NcoI and NotI, respectively. The expression vector, pET(AT)FVO, was prepared by digesting pET (AT)PfMSP-$1_{42}$ (3D7) (Angov et. al. (2003) Molec Biochem. Parasitol; in press) and the MSP-$1_{42}$ (FVO) PCR fragment, with NcoI and NotI. The digested DNA's were purified by agarose gel extraction (QIAEXII, Qiagen, Chatsworth, Calif.), ligated with T4 DNA ligase (Roche Biochemicals) and transformed into *E. coli* BL21 DE3 ($F^-$ ompT $hsdS_B$ ($r_B^- m_B^-$) gal dcm (DE3) [Invitrogen, Carlsbad, Calif.] (Maniatis). Two clones were sequenced and found to be identical in this region to Genbank Accession number, L20092. In preparing the final expression construct, two overlapping fragments of the MSP-$1_{42}$ gene DNA that encoded a single base change at amino acid #158 (ATC to ATA) led to a synonymous amino acid substitution. The primer pairs used in the PCR reaction were designated FVO-PCR1 plus EA5 and FVO-PCR2 plus EA3,5'-TAAAAAATATATAAACGACAAAC-3' (SEQ ID NO:9) and 5'-AAAAGGGAAGATATTTCTCATTT-3 (SEQ ID NO:10), respectively. The base pair changes away from native sequence are underscored. In the first amplification, primers FVO-PCR1 and EA5 plus the plasmid containing the native MSP-$1_{42}$ (FVO) gene sequence were mixed together to amplify the N-terminus of MSP-$1_{42}$ containing the synonymous substitution. In the second amplification, primers FVO-PCR2 and EA3 were used to amplify the C-terminus of MSP-$1_{42}$. The two PCR products were purified by agarose gel extraction using a DNA extraction kit, QIAEX II (Qiagen). The two PCR purified products were mixed (1:1) and were used as the template for a final amplification to produce full-length MSP-$1_{42}$ using flanking primers FVO-PCR1 and FVO-PCR2. The final clone was prepared by digesting the vector DNA, pET(AT)PfMSP-$1_{42}$ (3D7), and insert DNA, with NcoI and NotI, and ligating together. The pET(AT)FVO.A plasmid encodes 17 non-MSP-1 amino acids including a hexa-histidine tag at the N-terminus of *P. falciparum* FVO strain MSP-$1_{42}$ sequence.

GMP Fermentation and Expression of MSP-$1_{42}$ (FVO) (FMP003). Based on conditions obtained from laboratory scale 10 L fermentations, a 300 L GMP fermentation containing Super Broth media supplemented with 15 μg/ml tetracycline was inoculated with 3 L of fresh stationary phase culture in accordance with Batch Production Record (BPR)-444-00. Fermentation continued at 37° C. until an $OD_{600}$ of 5.0-7.0 was reached. The culture temperature was reduced from 37° C. to 25° C. prior to induction of protein expression with 0.1 mM IPTG for 2.5 hours. At the end of the induction, cells were harvested by centrifugation at 27,666×g for 1 hr at 4° C. and the *E. coli* cell paste was stored at −80° C. in the Department of Biologics Research, Pilot Bioproduction Facility, WRAIR, Silver Spring, Md.

GMP Purification of *E. coli* expressed FMP003, BPR-444-00 Lot # 0792. Cell paste was lysed in buffer containing 0.01 M sodium phosphate, pH 6.2, 0.05 M sodium chloride, 0.08 M imidazole, 0.002 M magnesium chloride, and 50 U/ml benzonase. Following cell lyses by microfluidization, Tween 80 and sodium chloride were added to final concentrations of 1.0% (v/v) and 1.0 M, respectively, and the lysate was incubated on ice for 30 minutes with stirring prior to centrifugation at 27,666×g for 1 hr at 4° C. The clarified lysate was collected and filtered through 0.45 μm Millipore filters (Millipore). All subsequent steps were carried out at 4° C. A two-step chromatography was used to purify the MSP-$1_{42}$ (FVO) to near homogeneity.

$Ni^{+2}$ NTA Superflow (Qiagen, Chatsworth, Calif.): A column with a 12:1 w/v cell paste to resin ratio, was equilibrated with 0.01M sodium chloride, pH 6.2, 1.0M sodium chloride, 0.08M imidazole (Ni-buffer) supplemented with 1.0% Tween 80 (v/v) (NOF Corporation). Filtered lysate was applied to the column at a flow rate of 32 ml/min and washed with 20 column volumes of Ni-buffer containing 1.0% Tween 80. The column was washed with 20 volumes of 0.01M sodium phosphate, pH 6.2, 0.5M sodium chloride, 0.08M imidazole buffer containing 1.0% Tween 80 (v/v) and followed by 20 volumes of 0.01M sodium phosphate, pH 8.5, 0.075M sodium chloride, 0.02M imidazole. MSP-1$_{42}$ (FVO) was eluted by using 5 column volumes of 0.01M sodium phosphate, pH 8.5, 0.075M sodium chloride, 1M imidazole and 0.2% Tween 80.

Q Sepharose chromatography: Q Sepharose Fast Flow [Amersham-Pharmacia, Milwaukee, Wis.] (cell paste: resin ratio=12:1 w/v), was equilibrated with 0.01 M Glycine, pH 9.6, 0.035 M sodium chloride, 0.002 M EDTA and 0.2% Tween 80 (Q-buffer). The imidazole eluted MSP-1$_{42}$ from the preceding step was diluted with an equal volume of 0.01 M Glycine, pH 9.6, 0.004 M EDTA and 0.2% Tween 80 and the pH was adjusted to 9.6 by addition of 1N sodium hydroxide. The diluted sample was applied at a flow rate of 65 ml/min to the Q-column and washed with 5 column volumes of Q-buffer. The column was washed with 30 column volumes at a flow rate of 82 ml/min. The MSP-1$_{42}$ (FVO) was eluted with 3 column volumes of 0.01 M sodium phosphate, pH 7.2, 0.2 M sodium chloride, 0.002 M EDTA and 0.2% Tween 80. Using ultrafiltration with an UFP-3C-6A (MWCO 3K) (A/G Technology, Needham, Mass.), the eluted MSP-1$_{42}$ (FVO) was concentrated two-fold to approximately 0.5 mg/ml and the buffer was exchanged with 10 volumes of 0.0017 M potassium phosphate (monobasic), 0.005 M sodium phosphate (dibasic), 0.15M sodium chloride, 0.1% Tween 80, pH 7.1. The MSP-1$_{42}$ (FVO) was filter sterilized through a Millipak 60 0.22-μm filtration unit and the final purified bulk was stored at −80° C.

Formulation for use with GSK adjuvant, ADJUVANT B. The purified bulk MSP-1$_{42}$ was mixed with 0.05 M sodium phosphate, 15.75% lactose (w/v) and Tween 80, to make a final concentration of 100 ug/ml MSP-1$_{42}$, 0.0235 M sodium phosphate, 3.15% lactose, 0.2% Tween 80 (final). Formulated MSP-1$_{42}$ (FVO), BPR-446-01 Lot 0818, was sterile filtered through a Millipak 40 0.22-μm filtration unit and added to 3 ml glass vials for lyophilization as described in the Batch Production Record, BPR-443-01. The final container vials were sealed with Lyo stoppers and metal crimps and stored at −20° C., BPR-443-01, Lot 0817.

SDS-PAGE and Immunoblotting. MSP-1$_{42}$ (FVO) product was separated by Tris-Glycine SDS-PAGE under non-reducing or reducing (10% 2-mercaptoethanol) conditions. Total protein was detection by Coomassie Brilliant Blue R-250 (Bio-Rad Laboratories, Hercules, Calif.) staining and immunoblotting are as previously described (Angov et al., 2003, supra). Nitrocellulose membranes were probed with either polyclonal mouse anti-FVO MSP-1$_{42}$ antibodies (a gift from Dr. Sanjai Kumar, FDA, Bethesda, Md.), polyclonal rabbit anti-*E. coli* antibodies (GSK) or mouse mAbs diluted into PBS, pH 7.4 containing 0.1% Tween 20. The mAbs used for evaluation of proper epitope structure included 2.2 (McBride et al, 1987, Mol. Biochem. Parasitol., 23, 71-84; Hall et al, 1983, Mol. Biochem. Parasitol, 7, 247-65), 12.8 (McBride, 1987, supra; Blackman et al, 1990, J. Exp. Med., 172, 379-82), 7.5 (McBride, 1987, supra; Hall et al, 1983, supra), 12.10 (McBride, 1987, supra; Blackman et al, 1990, supra), 5.2 (Chang et al, 1988, Exp. Parasitol., 67, 1-11).

Potency in mice. Potency studies were performed in female Balb/C mice vaccinated with 1.0, 0.3 and 0.1 ug of MSP-1$_{42}$ (FVO) in Adjuvant B diluted with sterile PBS. The vaccine was prepared by constituting a single vial with Adjuvant B (100 μg/ml) followed by dilution with sterile PBS to make the final 1.0, 0.3 and 0.1 ug doses. The mice were immunized subcutaneously with 100 μl of MSP-1$_{42}$ (FVO) vaccine in the inguinal area and bled after 28 days. The pre- and post-immune sera were analyzed against yMSP-1$_{19}$ coated plates by ELISA and the results were reported as the serum dilution that gives an absorbance of 1.0 OD$_{414}$ (Stoute et al, 1997, N. Engl. J. Med., 336, 86-91). Mice were considered seropositive if the following criteria were met:

(ELISA Units-3SD)$_{post-vaccination}$−(ELISA Units+3SD)$_{pre-vaccination}$>0

Inhibition of Parasite Invasion by Immune Sera. Female, New Zealand white rabbits were vaccinated four times subcutaneously with the MSP-1$_{42}$ emulsified in Complete Freund's Adjuvant (CFA) for their first immunization followed by Incomplete Freund's Adjuvant (FIA) for all subsequent immunizations at 3, 6 and 9 weeks. Pre- and post-immune sera were prepared prior to the first immunization and two weeks following the final immunization, respectively. For the invasion inhibition assay, sera were adsorbed with human A+ RBC and then dialyzed against RPMI 1640 adjusted to pH 7.4 with sodium hydroxide and added to settled 100 μl cultures of synchronous *P. falciparum* (FVO strain) schizont-infected erythrocytes (3-5 nuclei) at 2% hematocrit and 0.25% parasitemia. Static and suspension invasion assays were performed as described previously (Haynes et al, 2002, Methods, Mol. Med., 72, 535-54). Invading parasites were quantified by flow cytometry by staining with 1 μM Bisbenzimide Hoechst 33342 trihydrochloride (Sigma, St. Louis, Mo.) followed by dilution into PBS-EDTA. The dye was excited at 325 nm and the emitted light was detected at 530 nm. A total of 40,000 erythrocytes were counted by forward scatter.

Processing Inhibition Assay. Merozoites (Mz), prepared from cultures of schizont-infected red blood cells (iRBC) (7-9 nuclei) enriched on Percoll and returned to culture for 4 h, were purified as described and stored at −70° C. until use. Purified Mz were thawed on ice, washed with Wash Buffer (WB; PBS containing 10 μg/ml each antipain, aprotinin, and leupeptin and 100 μM tosyl-lysyl-chloromethyl ketone), centrifuged at 20,000×g for 5 min and resuspended in WB. PIA reactions were assembled on ice in pre-chilled tubes in WB with 0.001 M magnesium chloride and 0.001 M calcium chloride. Samples included a negative control (WB), which allowed processing; a positive control (SDS, 0.001 M PMSF, or 4% v/v mAb 12.8), which inhibited processing; and unknowns (4% v/v serum). Each assay contained Mz from approximately 3×10$^6$ PRBC. Reactions were incubated at 37° C. for a h and were stopped by adding an equal volume of 2×SDS-PAGE sample buffer.

Western blots were reacted with biotin-labeled rabbit anti-MSP1$_{42}$, followed by AP-Streptavidin conjugate (Promega) and visualized with BCIP and NBT.

*Aotus nancymai*. Spleen intact *Aotus nancymai* of either sex with no history of *Plasmodium* species infections as determined by parasitological and serological examinations. Monkeys used weighed no less than 700 grams at the start of the study. Through physical and blood hematological and clinical chemistry values, the monkeys were determined to be in general good health and free of tuberculosis (TB). Monkeys that met the inclusion criteria were stratified according to their weight and were further stratified according to sex. Monkeys were randomly assigned to the vaccine or control group through a table of random numbers. Based on results from previous studies using FVO strain *P. falciparum* in *A. nancymai* and the uniformity of their infections, a minimum of 6 animals per group was required to guarantee a>80% power to detect a 50% difference in efficacy of a vaccine. The monkeys were housed singly or as mate pairs. Space recommendations for laboratory animals were as stated in the *Guide for the Care of Laboratory Animals, NIH*. Monkeys were fed a diet that provides adequate nutrition and calories.

Immunization of *Aotus* Monkey The experimental group was immunized with 50 μg of the *E. coli* expressed recombinant FVO protein emulsified in CFA and FIA (Difco Laboratories, Irvine, Calif.) for the first and second immunizations, respectively. The CFA contained 0.5 mg/ma of heat-killed *Mycobacterium butycum* in paraffin oil base or just the paraffin oil base for FIA. The inoculants were made up to and having no more than a total volume of 0.5 ml. The hair was closely shaved over the back region of the monkeys to allow visualization of any reactions and the formulation was given subcutaneously in four sites of ~125 µl per injection site. The second dose was given in the same manner as the first. The control group was immunized with an unrelated *P. vivax* protein (Pvs25) formulated in the same adjuvant as the experimental group. Immunizations were made on day 0 and 6-7 weeks following the first immunization. Not all the monkeys were immunized on the same day for the second immunization due to a strong reaction against the first immunization.

Challenge strain. The *P. falciparum* Vietnam Oak Knoll (FVO) that has been adapted to karytype I *Aotus* monkeys and produces reproducible rapid density parasitemia in spleen intact naïve monkeys was used for the challenge infection. Parasitized erythrocytes were obtained from an *A. nancymai* monkey and diluted in sterile RPMI-1640 tissue culture media to obtain 10,000 parasitized erythrocytes per 0.5 ml. The inoculum was administered intravenously via the femoral vein.

Parasite Counts. Beginning on day 3 following challenge, daily blood smears were made using the Earle-Perle technique to quantify parasites per µl of blood and were stained with the standard Giemsa methodology. When parasite counts reached a level of >80,000/µl of blood, the parasite density was determined from a thin smear as the percentage of erythrocytes infected by counting the number of parasites per 1000 erythrocytes. Parasitemia was measured for 56 days. Monkeys that developed high-density parasitemia (>5% or 200,000 parasites/41 of blood) were treated with mefloquine (Roche Laboratories, Nutley, N.J.) and quinine (Marion Merrel Dow, Inc., Kansas City, Kans.). Monkeys were treated for anemia by iron supplementation or transfusion of whole blood if there was a decrease below 20% packed cell volume or less than 50% of baseline values. All trial animals were followed parasitologically by daily blood smears and observation at least 4 weeks before immunization, during immunization and for 56 days following challenge. Observations on local and/or systemic reactions such as abscesses, necrotic lesions, anorexia and weight loss were made at least once per week.

Collection of blood for hematology and blood chemistry. Bi-weekly collections of not more than 5% of a monkeys total blood volume (based on a total volume calculation of 66 ml/kg body weight) were made by venipuncture of the femoral vein. 44 µl of blood was used for a complete blood count: erythrocytes/µl, leukocytes/µl, hematocrit, hemoglobin concentration, platelets/µl, MCH, MCV, MCHC, and a leukocyte differential. The remaining blood was processed for serum.

Statistical analysis. Maximum parasitemia, cumulative parasitemia, prepatent period, day of maximum parasitemia, and days to 100 parasites/µl were analyzed for significant differences by the Wilcoxin-Rank Sum Test.

Trial Masking. Persons responsible for the reading of blood smears for parasitemia determinations, serological testing, specimen collection, for examination and provision of health care, and the statistical analysis of the data did not know the experimental groups to which animals were assigned. The code was not broken until the collection of the parasitological data was completed.

EXAMPLE 1

Figure 1B:
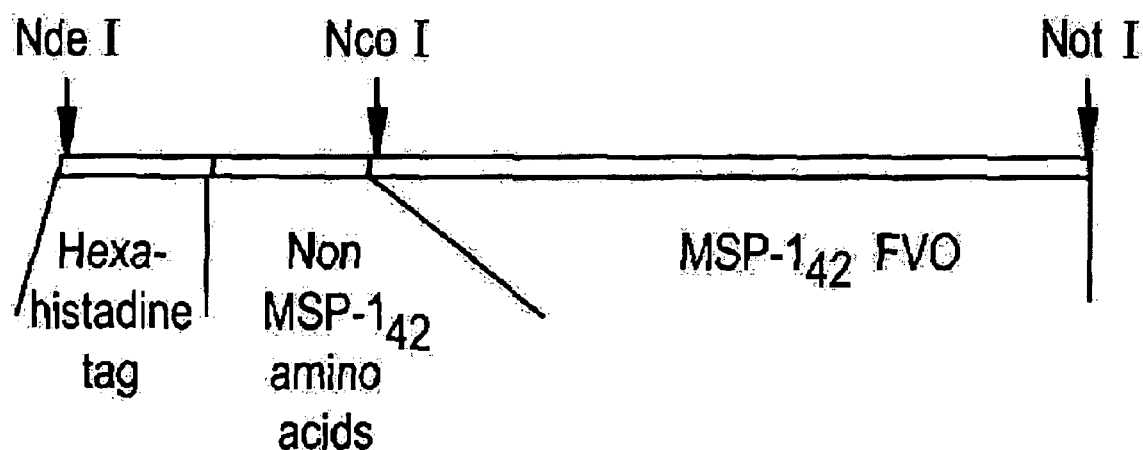
Figure 1C:
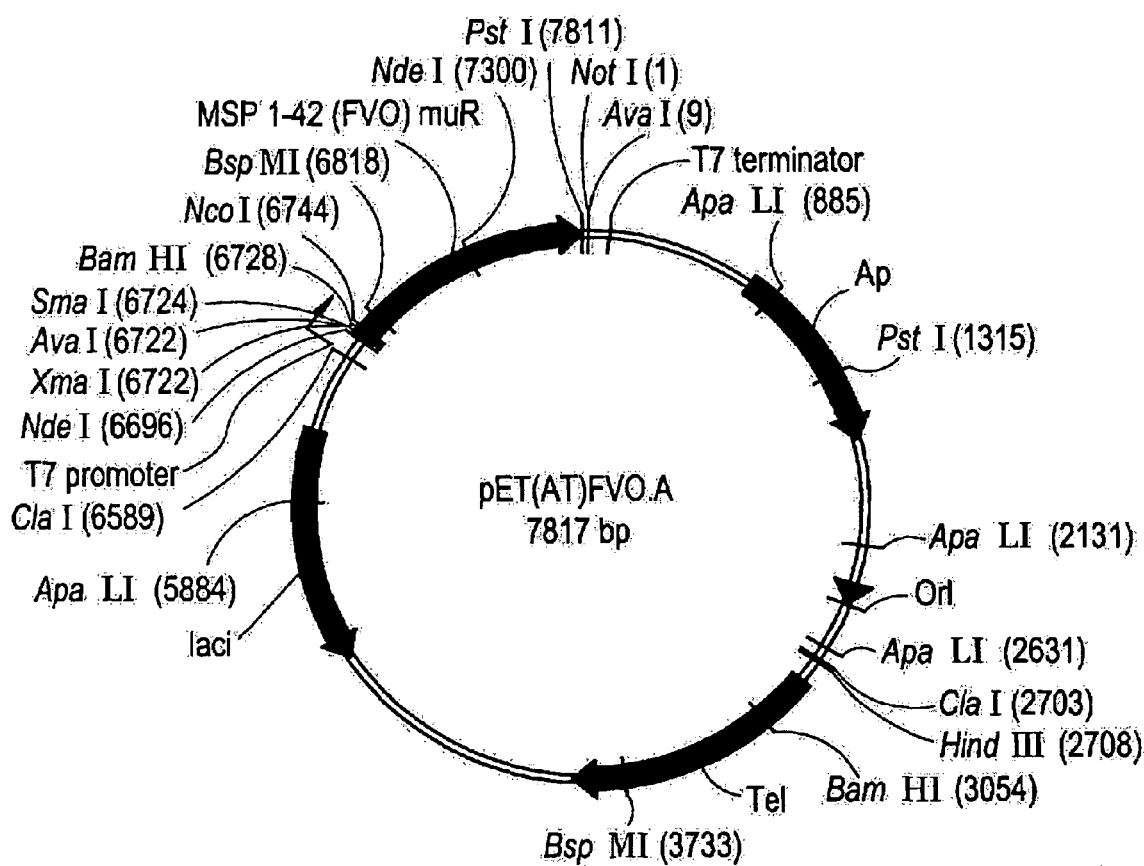
Figure 1D:
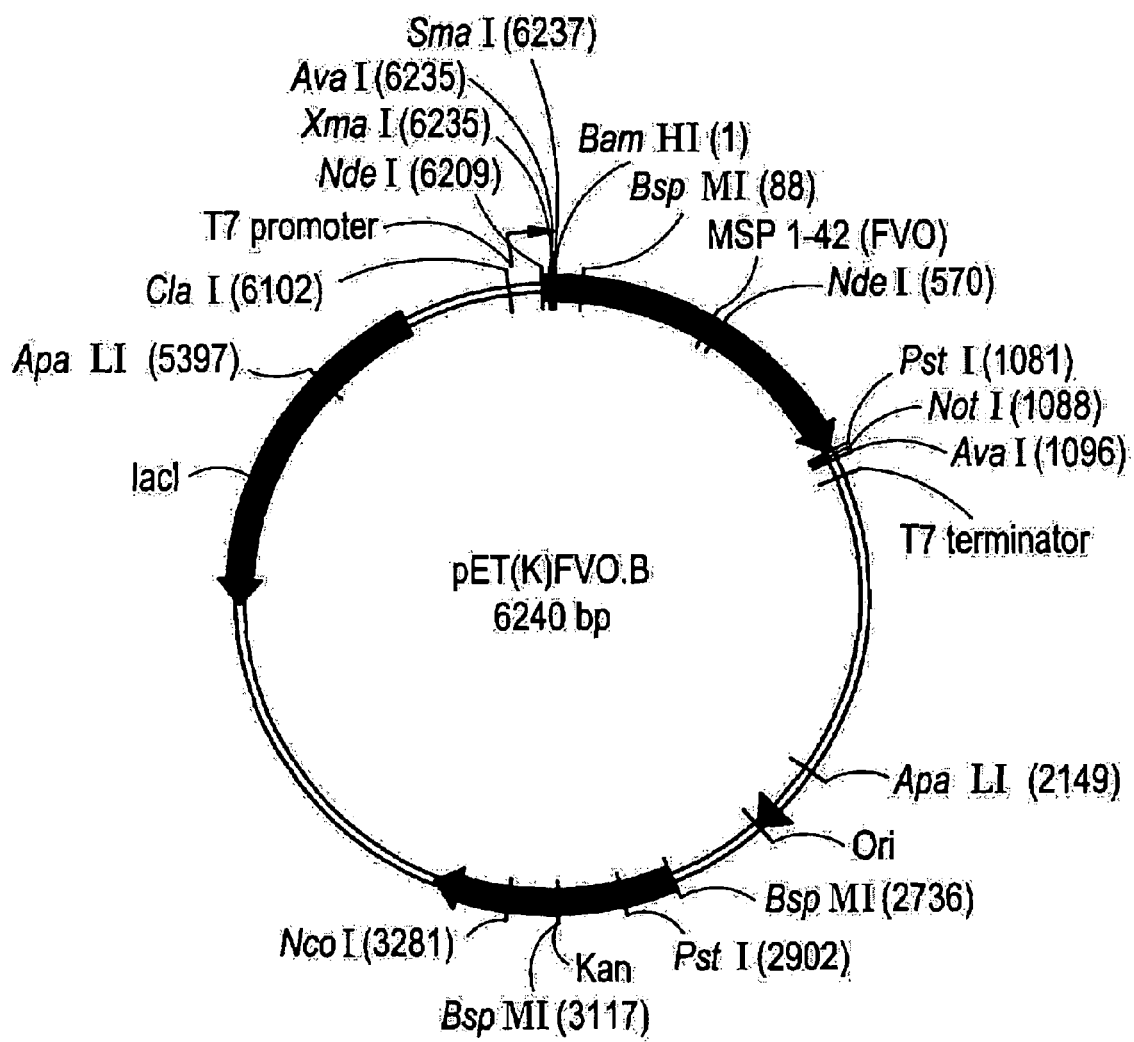
Figure 1E:
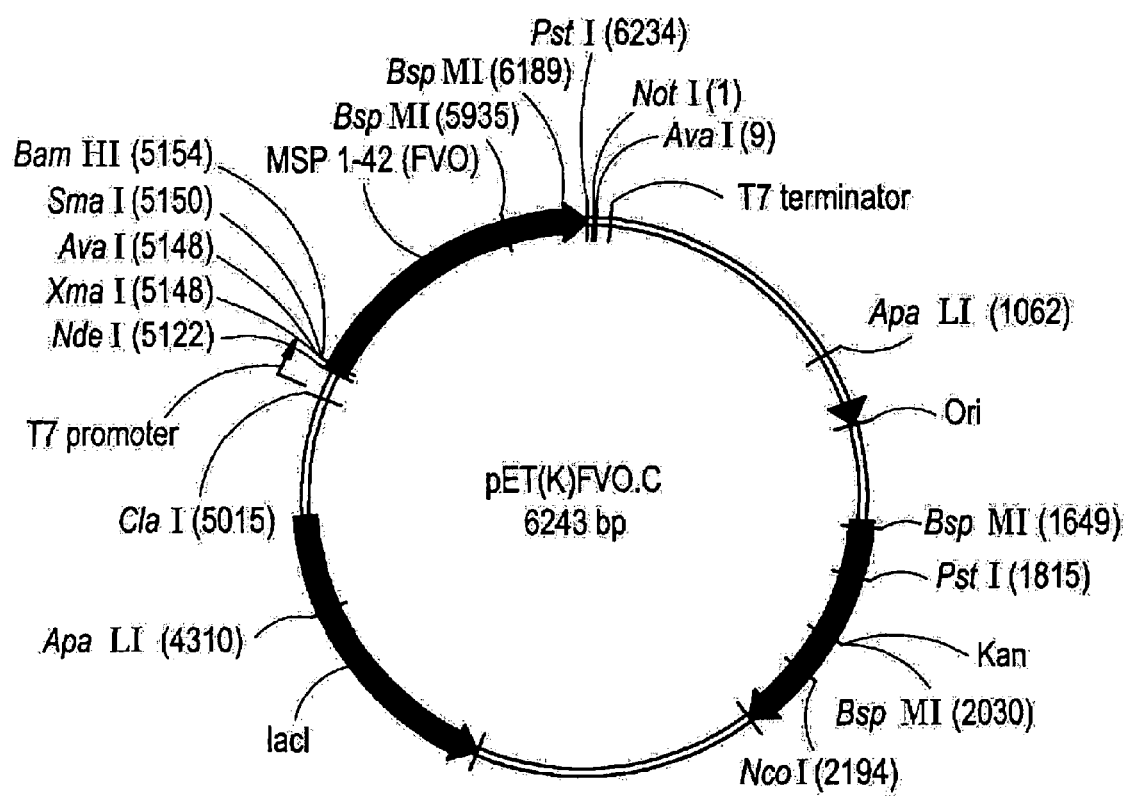
Figure 2:
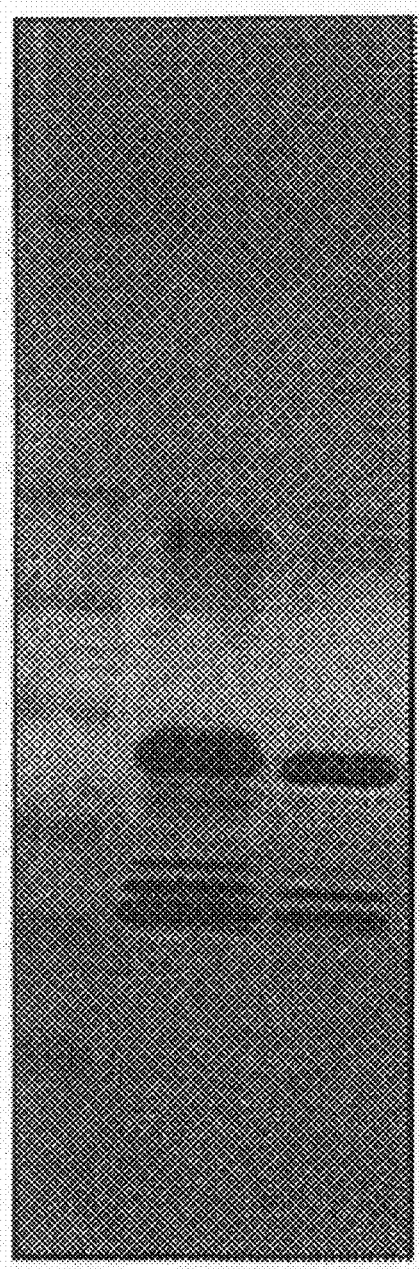
FIG. 2: Immunoblot. Immunoblotting of partially purified MSP-$1_{42}$ (FVO); $Ni^{2+}$ NTA column (lane 2) and Q Sepharose (lane 3) electrophoresed under non-reducing conditions. The blot was probed with polyclonal mouse anti-MSP-$1_{42}$ (FVO) antibodies raised against *P. falciparum* FVO strain DNA vaccine candidate.

The *E. coli* expressed MSP-1$_{42}$ fragment is comprised from amino acid 1349 (Ala) to amino acid 1713 (Ser) from the full length *P. falciparum* FVO MSP-1. The MSP-1$_{42}$ DNA used to prepare this clone was produced by PCR amplification of *P. falciparum* FVO genomic DNA; and the fragment was subcloned into the expression vector, pET(AT)PfMSP-1$_{42}$ (3D7), that was previously described for the expression of the MSP-1$_{42}$ 3D7 allele, (Angov et. al. (2003) Molec Biochem. Parasitol; in press) (FIG. 1A). The final product contains 17 non-MSR-1$_{42}$ amino acids that include the hexa-histidine tag for Ni$^{+2}$ chelating chromatography at the N-terminus (FIG. 1B). Soluble expression of MSP-1$_{42}$ was induced by addition of 0.1 mM IPTG. MSP-1$_{42}$ was purified under GMP conditions using a two-step chromatographic method; that included a Ni$^{+2}$-NTA Sepharose affinity resin followed by a Q-Sepharose ion exchanger. The purified bulk was concentrated and buffer exchanged using ultrafiltration. The final protein was purified to greater than 95% of MSP-1. Purity profiles by SDS-PAGE/Coomassie Blue staining revealed a doublet at about 42 kDa, a 30 kDa proteolytic fragment and some high molecular weight aggregates (FIG. 3A). Blots probed with either polyclonal mouse anti-MSP-1$_{42}$ (FVO) or with rabbit anti-*E. coli* antibodies revealed that all Coomassie Blue detectable bands were derived from MSP-1. The 30 kDa and several other minor truncated forms of MSP-1$_{42}$ reacted with the polyclonal mouse anti-MSP-1$_{42}$ (FVO) antibodies (FIG. 2, lanes 2 and 3) however; these same fragments did not react with the polyclonal rabbit anti-*E. coli* antibodies. (Data not shown). Further evaluation of the 30 kDa fragment by N-terminal sequence analysis revealed that this fragment contained an identical amino acid sequence to the first 24 amino acids of the N-terminus of MSP-1$_{42}$ thus suggesting truncation at the C-terminus of MSP-1$_{42}$. The final product was characterized for correct structure by immunoblot detection under non-reducing and reducing conditions against disulfide-dependent MSP-1$_{42}$ specific mAbs (FIG. 3). The SDS-denatured, non-reduced MSP-1$_{42}$ migrated as a doublet (FIG. 3A, lanes 2, 3 and 4) however following reduction of disulfide bridges with 2-mercaptoethanol, the doublet was reduced to a single major monomer that migrated at approximately 50 kDa and some reduction-resistant fragments visible at approximately 90 and 30 kDa (FIGS. 3E, F, G & H, lanes 2 and 3). MSP-1$_{19}$ specific mAbs 12.10 (FIG. 3B, non-reduced, lanes 2, 3 & 4; FIG. 3F, reduced, lanes 2 & 3) and 12.8 (FIG. 3C, non-reduced, lanes 2, 3 & 4; FIG. 3G, reduced, lanes 2 & 3) reacted very strongly with the MSP-1$_{42}$ under non-reducing conditions; however, disulfide bridges reduction nearly eliminated all reactivity to these fragments. Monomeric MSP-1$_{42}$ as well as high molecular weight aggregates reacted against the conformation-sensitive mAb 5.2.

Mice vaccinated with MSP-1$_{42}$ and ADJUVANT B adjuvant, seroconverted to MSP-1$_{42}$ positive antibodies as measured by ELISA. All doses of MSP-1$_{42}$ tested in Balb/c mice, 1.0, 0.3 and 0.1 µg, induced MSP-1 positive antibodies at 100, 60 and 30%, respectively, following a single immunization.

Rabbits vaccinated with MSP-1$_{42}$ in CFA/FIA adjuvant, induced antibody specificities that inhibited parasite growth in vitro at 70% and 46% in homologous suspension cultures, and at 58% and 39% in homologous static cultures, for rabbit 02A and 02B, respectively. The invasion inhibition observed for the static culture was only slightly less than that observed for the suspension culture (Table 1).

TABLE I

Rabbit Anti-MSP1$_{42}$ (FVO)/CFA Sera are Inhibitory to *P. falciparum* Invasion In vitro

| Rabbit | Mean Inhibition vs Pre-Immune Serum (Standard Deviation) | |
|---|---|---|
| | Suspension Culture | Static Culture |
| 02A | 70% (9%) | 58% (10%) |
| 02B | 46% (10%) | 39% (7%) |

Two rabbits, O2A and O2B were immunized 4 times subcutaneously with *E. coli* expressed recombinant *P. falciparum* FVO strain MSP-1$_{42}$ constituted in either complete Freund's adjuvant (CFA) for the first immunization or in incomplete Freund's adjuvant (IFA) for all subsequent immunizations. The rabbits were ex-sanguinated 2 weeks following the last immunization. Sera were prepared as described in Materials and Methods. The initial parasitemia was 0.25% and the cultures were maintained for 48 hours. The percent invasion inhibition was quantified by flow cytometry as described in the Materials and Methods. The data are reported as the mean of triplicates and the standard deviations in parentheses.

TABLE 2

Effect of Vaccination on Parasitemia in *Aotus nancymai*

| Group | Monkey n | Prepatent Day | Day 11 Cumulative Parasitemia/µl | Maximum parasetemia | Peak Day | Chemotherapy for parasetemia |
|---|---|---|---|---|---|---|
| Pv25 | 5 | 6.6 | 61,266 | 302,000 | 13.4 | 5/5 |
| FVO | 6 | 13.8 | 118 | 7,855 | 22.2 | 0/6 |

Total number of monkeys was 5 and 6 for the control (Pvs25) and experimental group (MSP-1$_{42}$ (FVO)), respectively. One monkey from the control group died before the second immunization. Parasitemia is reported as the number of parasitized erythrocytes per µl of blood. All of the monkeys in the control group were treated with mefloquine.

All *Aotus* monkeys used in this study were found to be in general good health and had no history of *Plasmodium* species infection as determined by serological analyses. They were found to be free of TB. The monkeys received 50 µg/ml of MSP-1$_{42}$ constituted in CFA and FIA adjuvant for the first and second immunizations, respectively. Some of the monkeys reacted strongly to the primary immunization and therefore, the second immunization was delayed by 5-7 days, however, the veterinarians in the study determined that vaccination with MSP-1$_{42}$ did not affect the overall health of these monkeys. One monkey in the control group died prior to the day of second immunization. Autopsy results showed that this death was not related to the previous immunization.

Seven weeks following the second immunization all of the monkeys were challenged with 10,000 *P. falciparum* FVO strain parasitized erythrocytes in 0.5 ml. The challenge inoculum was administered intravenously via the femoral vein. The mean prepatent day the control (Pvs25/CFA/FIA) and the experimental (MSP-1$_{42}$/CFA/FIA) group were 6.6 and 13.8 days, respectively (Table 2). By day 14 (FIG. 4A), all monkeys in the control group had to be treated for high parasitemia. The mean maximum parasite count for the control group was 302,000/µl. However, none of the MSP-1$_{42}$/CFA vaccinated animals had to be treated for parasitemia (FIG. 4B). The mean maximum parasitemia for the MSP-1$_{42}$/CFA group was 7,855 parasites/µl. The mean maximum parasite count for the control group was about 40 times higher than that detected for the experimental group. Using the Wilcoxon Rank Test, significant differences (>0.004) were observed between the mean prepatent days and maximum parasite counts for the two groups. Sera from an *Aotus* monkey immunized with MSP1-42 (FVO)/Complete Freund's adjuvant was tested in a secondary-processing inhibition assay (PIA). This assay measures the ability of antibodies to inhibit the conversion of MSP1-42 (p42) to MSP1-33 (p33) and MSP1-19 (p19) from purified merozoites. The negative control for inhibition of secondary processing is incubation of merozoites with PMSF, this lane reveals weakly detectable levels of MSP1-33. The invasion inhibitory mAb 12.8, which inhibits parasite growth in vitro also, inhibits the secondary processing of p42 to p33. Pre-immune sera allows secondary processing to occur to form p33, while sera from day of challenge (DOC) and 6 weeks post challenge (DOC+6wk) inhibited the amount of the secondary processing to form p33. (FIG. 5)

Discussion

This study describes the processes developed for the manufacture and testing of a clinical grade *E. coli* expressed MSP-1$_{42}$ (FVO) in *Aotus* monkeys. The MSP-1$_{42}$ is highly purified and met all FDA standards for purity and safety required for clinical testing. Residual endotoxin levels were significantly below the FDA acceptable levels (FDA; 350 EU/dose/70 kg human, for our two-step chromatography, 60 EU/dose/70 kg human). The protein is comprised of a greater proportion of monomeric form and a minor proportion of truncated MSP-1$_{30}$.

Immunity developed against *P. falciparum* infection is antibody-dependent as shown in studies in which passive transfer of immune IgG protected volunteers following parasite challenge {Cohen, et al, 1964, Nature, 192, 733-37) Egan et al, 1999, supra}. In mice, the MSP-1$_{42}$ constituted with ADJUVANT B, the GSK adjuvant approved for clinical testing induced antibody specificities to MSP-1 following a single immunization. Sera from rabbits immunized with MSP-1$_{42}$/CFA inhibited *P. falciparum* growth in culture. These results suggest that the antibodies against the MSP-1$_{42}$/CFA recognized epitopes on MSP-1 from *P. falciparum* FVO and 3D7 strain parasites. Immunoblotting data showed that the MSP-1$_{42}$ protein has correct disulfide bridging patterns as measured by reactivity with disulfide-dependent mabs raised against *P. falciparum* malaria parasites, including the biologically functional mAbs designated as either growth or invasion inhibitory (mAb 12. 10) (McBride et al, 1987, supra; Hall et al, 1983, supra) (mAb 12.8) (McBride et al, 1987, supra; Blackman et al, 1990, supra) and blocking inhibitory (mAb 7.5, 2.2)(McBride et al, 1987, supra; Hall et al, 1983, supra), (mAb 1E1) (Blackman et al, 1994, J. Exp. Med). Thus, the recombinant protein has some correct structure and vaccinating with this molecule can lead to the induction of some antibody specificities that may control invasion of erythrocytes by merozoites.

The *E. coli* expressed MSP-1$_{42}$ (FVO)/CFA vaccine was evaluated in *Aotus* monkey's for its ability to induce a protective effect. All monkeys vaccinated with the negative control Pvs25/CFA had to be treated for parasitemia following a normal course of infection. However, in the experimental group, MSP-1$_{42}$/CFA, none of the six-monkeys required treatment for parasitemia. Two of these monkeys did however require treatment for anemia and had to be withdrawn from the study prior to reaching the intended endpoint, controlling parasitemia. In previous studies in which Freund's adjuvant was used with recombinant MSP-1$_{42}$ FVO molecules expressed from either baculovirus or transgenic mice, limited protection was observed with at least three immunizations (Stowers, 2002, supra). Transgenic mice from these studies secreted either a native sequence *P. falciparum* FVO MSP-1$_{42}$ homologous to the challenge strain or secreted a mutated MSP-1$_{42}$ designed to eliminate the two putative N-glycosylation sites. Both milk-derived MSP-1$_{42}$ products were used to vaccinate *Aotus* monkeys, followed by challenge with the homologous *P. falciparum* FVO parasite. Vaccination with the glycosylated milk-derived MSP-1$_{42}$ conferred no protection compared to the adjuvant control. By contrast, vaccination with the non-glycosylated milk-derived MSP-1$_{42}$ resulted in 4/5 monkeys being protected from an otherwise lethal infection with *P. falciparum*. Immunization with a baculovirus-derived glycosylated form of MSP-1$_{42}$ protected five of seven monkeys from a lethal challenge. The authors concluded that the different vaccines tested had differing glycosylation patterns that had a critical role in determining efficacy. From our study we show that the *Aotus* monkeys were protected after only two immunizations at seven-week intervals followed by homologous challenge seven weeks later. We believe that we have an appropriate model system to evaluate the efficacy of candidate *P. falciparum* FVO malaria antigens using CFA, however, the current climate against the use of Freund's adjuvant in non-human primates may preclude further evaluation of these antigens in *Aotus* monkeys. Future studies and focus must be directed toward the development and characterization of new adjuvants that can induce protective immunity without inducing any severe side effects and that will be suitable for human clinical testing.

What is claimed is:

1. An isolated recombinant vector comprising a DNA sequence encoding MSP-1$_{42}$ wherein said DNA sequence is SEQ ID NO:4.

2. An isolated host cell transformed with the vector according to claim 1.

3. The vector of claim 1 wherein said vector is pET(AT)FVO.C.

4. An isolated host cell transformed with the vector of claim 3.

* * * * *

SEQUENCE LISTING

```
<160> NUMBER OF SEQ ID NOS: 10

<210> SEQ ID NO 1
<211> LENGTH: 1119
<212> TYPE: DNA
<213> ORGANISM: Artificial Sequence
<220> FEATURE:
<223> OTHER INFORMATION: Description of Artificial Sequence:
      P. falciparum (FVO) MSP1-42 (Mut 7, Pause Site mutant)
<220> FEATURE:
<221> NAME/KEY: CDS
<222> LOCATION: (1)..(1116)

<400> SEQUENCE: 1 atg gca cac cat cat cat cat ccc ggg gga tcc ggt tct ggt acc        48
Met Ala His His His His His Pro Gly Gly Ser Gly Ser Gly Thr
  1               5                  10                  15 atg gca gta act cct tcc gta att gat aac ata ctt tct aaa att gaa    96
Met Ala Val Thr Pro Ser Val Ile Asp Asn Ile Leu Ser Lys Ile Glu
             20                  25                  30 aat gaa tat gag gtt tta tat tta aaa cct tta gca ggt gtt tat aga   144
Asn Glu Tyr Glu Val Leu Tyr Leu Lys Pro Leu Ala Gly Val Tyr Arg
         35                  40                  45 agt tta aaa aaa caa tta gaa aat aac gtt atg aca ttt aat gtt aat   192
Ser Leu Lys Lys Gln Leu Glu Asn Asn Val Met Thr Phe Asn Val Asn
     50                  55                  60 gtt aag gat att tta aat tca cga ttt aat aaa cgt gaa aat ttc aaa   240
Val Lys Asp Ile Leu Asn Ser Arg Phe Asn Lys Arg Glu Asn Phe Lys
 65                  70                  75                  80 aat gtt tta gaa tca gat tta att cca tat aaa gat tta aca tca agt   288
Asn Val Leu Glu Ser Asp Leu Ile Pro Tyr Lys Asp Leu Thr Ser Ser
                 85                  90                  95 aat tat gtt gtc aaa gat cca tat aaa ttt ctt aat aaa gaa aaa aga   336
Asn Tyr Val Val Lys Asp Pro Tyr Lys Phe Leu Asn Lys Glu Lys Arg
            100                 105                 110 gat aaa ttc tta agc agt tat aat tat att aag gat tca ata gat acg   384
Asp Lys Phe Leu Ser Ser Tyr Asn Tyr Ile Lys Asp Ser Ile Asp Thr
        115                 120                 125 gat ata aat ttt gca aat gat gtt ctt gga tat tat aaa gta tta tcc   432
Asp Ile Asn Phe Ala Asn Asp Val Leu Gly Tyr Tyr Lys Val Leu Ser
    130                 135                 140
```

```
gag aaa tat aaa tca gat tta gat tca att aaa aaa tat ata aac gac        480
Glu Lys Tyr Lys Ser Asp Leu Asp Ser Ile Lys Lys Tyr Ile Asn Asp
145                 150                 155                 160 aaa caa ggt gaa aat gag aaa tac ctt ccc ttt tta aac aat att gag        528
Lys Gln Gly Glu Asn Glu Lys Tyr Leu Pro Phe Leu Asn Asn Ile Glu
                165                 170                 175 acc tta tat aaa aca gtt aat gat aaa att gat tta ttt gta att cat        576
Thr Leu Tyr Lys Thr Val Asn Asp Lys Ile Asp Leu Phe Val Ile His
            180                 185                 190 tta gaa gca gaa gtt cta aat tat aca tat gag aaa tca aac gta gaa        624
Leu Glu Ala Glu Val Leu Asn Tyr Thr Tyr Glu Lys Ser Asn Val Glu
        195                 200                 205 gtt aaa ata aaa gaa ctt aat tac tta aaa aca att caa gac aaa ttg        672
Val Lys Ile Lys Glu Leu Asn Tyr Leu Lys Thr Ile Gln Asp Lys Leu
    210                 215                 220 gca gat ttt aaa aaa aat aac aat ttc gtt gga att gct gat tta tca        720
Ala Asp Phe Lys Lys Asn Asn Asn Phe Val Gly Ile Ala Asp Leu Ser
225                 230                 235                 240 aca gat tat aac cat aat aac tta ttg aca aag ttc ctt agt aca ggt        768
Thr Asp Tyr Asn His Asn Asn Leu Leu Thr Lys Phe Leu Ser Thr Gly
                245                 250                 255 atg gtt ttt gaa aat cct gct aaa acc gtt tta tct aat tta ctt gat        816
Met Val Phe Glu Asn Pro Ala Lys Thr Val Leu Ser Asn Leu Leu Asp
            260                 265                 270 gga aac ttg caa ggt atg tta aac att tca caa cac caa tgc gta aaa        864
Gly Asn Leu Gln Gly Met Leu Asn Ile Ser Gln His Gln Cys Val Lys
        275                 280                 285 aaa caa tgt cca caa aat tct gga tgt ttc aga cat tta gat gaa aga        912
Lys Gln Cys Pro Gln Asn Ser Gly Cys Phe Arg His Leu Asp Glu Arg
    290                 295                 300 gaa gaa tgt aaa tgt tta tta aat tac aaa caa gaa ggt gat aaa tgt        960
Glu Glu Cys Lys Cys Leu Leu Asn Tyr Lys Gln Glu Gly Asp Lys Cys
305                 310                 315                 320 gtt gaa aat cca aat cct act tgt aac gaa aat aat ggt gga tgt gat       1008
Val Glu Asn Pro Asn Pro Thr Cys Asn Glu Asn Asn Gly Gly Cys Asp
                325                 330                 335 gca gat gcc aaa tgt acc gaa gaa gat tca ggt agc aac gga aag aaa       1056
Ala Asp Ala Lys Cys Thr Glu Glu Asp Ser Gly Ser Asn Gly Lys Lys
            340                 345                 350 atc aca tgt gaa tgt act aaa cct gat tct tat cca ctt ttc gat ggt       1104
Ile Thr Cys Glu Cys Thr Lys Pro Asp Ser Tyr Pro Leu Phe Asp Gly
        355                 360                 365 att ttc tgc agt taa                                                   1119
Ile Phe Cys Ser
    370

<210> SEQ ID NO 2
<211> LENGTH: 372
<212> TYPE: PRT
<213> ORGANISM: Artificial Sequence
<220> FEATURE:
<223> OTHER INFORMATION: Description of Artificial Sequence:
      P. falciparum (FVO) MSP1-42 (Mut 7, Pause Site mutant)

<400> SEQUENCE: 2

Met Ala His His His His His His Pro Gly Gly Ser Gly Ser Gly Thr
 1               5                  10                  15

Met Ala Val Thr Pro Ser Val Ile Asp Asn Ile Leu Ser Lys Ile Glu
                20                  25                  30

Asn Glu Tyr Glu Val Leu Tyr Leu Lys Pro Leu Ala Gly Val Tyr Arg
```

```
                35                  40                  45
Ser Leu Lys Lys Gln Leu Glu Asn Asn Val Met Thr Phe Asn Val Asn
    50                  55                  60

Val Lys Asp Ile Leu Asn Ser Arg Phe Asn Lys Arg Glu Asn Phe Lys
65                  70                  75                  80

Asn Val Leu Glu Ser Asp Leu Ile Pro Tyr Lys Asp Leu Thr Ser Ser
                85                  90                  95

Asn Tyr Val Val Lys Asp Pro Tyr Lys Phe Leu Asn Lys Glu Lys Arg
            100                 105                 110

Asp Lys Phe Leu Ser Ser Tyr Asn Tyr Ile Lys Asp Ser Ile Asp Thr
        115                 120                 125

Asp Ile Asn Phe Ala Asn Asp Val Leu Gly Tyr Tyr Lys Val Leu Ser
    130                 135                 140

Glu Lys Tyr Lys Ser Asp Leu Asp Ser Ile Lys Lys Tyr Ile Asn Asp
145                 150                 155                 160

Lys Gln Gly Glu Asn Glu Lys Tyr Leu Pro Phe Leu Asn Asn Ile Glu
                165                 170                 175

Thr Leu Tyr Lys Thr Val Asn Asp Lys Ile Asp Leu Phe Val Ile His
            180                 185                 190

Leu Glu Ala Glu Val Leu Asn Tyr Thr Tyr Glu Lys Ser Asn Val Glu
        195                 200                 205

Val Lys Ile Lys Glu Leu Asn Tyr Leu Lys Thr Ile Gln Asp Lys Leu
    210                 215                 220

Ala Asp Phe Lys Lys Asn Asn Phe Val Gly Ile Ala Asp Leu Ser
225                 230                 235                 240

Thr Asp Tyr Asn His Asn Asn Leu Leu Thr Lys Phe Leu Ser Thr Gly
                245                 250                 255

Met Val Phe Glu Asn Pro Ala Lys Thr Val Leu Ser Asn Leu Leu Asp
            260                 265                 270

Gly Asn Leu Gln Gly Met Leu Asn Ile Ser Gln His Gln Cys Val Lys
        275                 280                 285

Lys Gln Cys Pro Gln Asn Ser Gly Cys Phe Arg His Leu Asp Glu Arg
    290                 295                 300

Glu Glu Cys Lys Cys Leu Leu Asn Tyr Lys Gln Glu Gly Asp Lys Cys
305                 310                 315                 320

Val Glu Asn Pro Asn Pro Thr Cys Asn Glu Asn Asn Gly Gly Cys Asp
                325                 330                 335

Ala Asp Ala Lys Cys Thr Glu Glu Asp Ser Gly Ser Asn Gly Lys Lys
            340                 345                 350

Ile Thr Cys Glu Cys Thr Lys Pro Asp Ser Tyr Pro Leu Phe Asp Gly
        355                 360                 365

Ile Phe Cys Ser
    370

<210> SEQ ID NO 3
<211> LENGTH: 1116
<212> TYPE: DNA
<213> ORGANISM: Artificial Sequence
<220> FEATURE:
<223> OTHER INFORMATION: Description of Artificial Sequence:
      P. falciparum (FVO) MSP1-42 (N-terminal Mod, initiation complex)

<400> SEQUENCE: 3
atggcacacc atcatcatca tcatcccggg ggatccggtt ctggtaccgc agttactcca      60
tctgttattg ataatattct ttctaaaatt gaaaacgaat atgaggtttt atatttaaaa     120
```

```
cctttagcag gtgtttatag aagtttaaaa aaacaattag aaaataacgt tatgacattt      180
aatgttaatg ttaaggatat tttaaattca cgatttaata aacgtgaaaa tttcaaaaat      240
gttttagaat cagatttaat tccatataaa gatttaacat caagtaatta tgttgtcaaa      300
gatccatata aatttcttaa taaagaaaaa agagataaat tcttaagcag ttataattat      360
attaaggatt caatagatac ggatataaat tttgcaaatg atgttcttgg atattataaa      420
gtattatccg agaaatataa atcagattta gattcaatta aaaaatatat aaacgacaaa      480
caaggtgaaa atgagaaata ccttcccttt taaacaata ttgagacctt atataaaaca      540
gttaatgata aaattgattt atttgtaatt catttagaag cagaagttct aaattataca      600
tatgagaaat caaacgtaga agttaaaata aagaactta attacttaaa aacaattcaa      660
gacaaattgg cagattttaa aaaaaataac aatttcgttg gaattgctga tttatcaaca      720
gattataacc ataataactt attgacaaag ttccttagta caggtatggt ttttgaaaat      780
cctgctaaaa ccgtttatc taatttactt gatggaaact tgcaaggtat gttaaacatt      840
tcacaacacc aatgcgtaaa aaaacaatgt ccacaaaatt ctggatgttt cagacattta      900
gatgaaagag aagaatgtaa atgtttatta aattacaaac aagaaggtga taaatgtgtt      960
gaaaatccaa atcctacttg taacgaaaat aatggtggat gtgatgcaga tgccaaatgt     1020
accgaagaag attcaggtag caacggaaag aaaatcacat gtgaatgtac taaacctgat     1080
tcttatccac ttttcgatgg tattttctgc agttaa                              1116

<210> SEQ ID NO 4
<211> LENGTH: 1116
<212> TYPE: DNA
<213> ORGANISM: Artificial Sequence
<220> FEATURE:
<223> OTHER INFORMATION: Description of Artificial Sequence:
      P. falciparum (FVO) MSP1-42 Full Gene Codon Harmonized

<400> SEQUENCE: 4
atggcacacc atcatcatca tcatcccggg ggatccggtt ctggtaccgc tgttacgcca       60
tcggttattg acaatatcct cagcaaaatt gaaaacgaat acgaggttct gtacctgaaa      120
ccactggctg gcgtttaccg ttctctgaaa aaacagctgg aaaacaatgt tatgaccttc      180
aacgttaacg ttaaggacat tctgaacagc cgcttcaaca acgcgaaaa ctttaaaaac      240 gttctggaaa gcgaccctga tccatacaaa gacctgacca gctctaacta cgttgtcaaa      300
gacccataca aattcctcaa caagaaaaa cgtgacaaat ttctgtcgtc ttacaactac      360
attaaggaca gcatcgacac ggacatcaac ttcgctaacg acgttctcgg ctactacaaa      420
atcctgtcgg aaaatacaa aagcgacctg gacagcatta aaaatacat taatgataaa      480 cagggcgaaa acgagaaata tctcccttc ctgaataaca ttgagacgct gtacaaaacc      540
gttaacgaca aaattgacct gttcgttatt cacctggaag ctaagttct caactacacc      600 tacgagaaaa gcaatgttga agttaaaatc aaagaactca actatctgaa aaccattcag      660
gataaactcg ctgacttcaa aaaaacaat aactttgttg gcattgctga cctgagcacc      720
gactacaatc acaacaatct gctcaccaag tttctctcta ccggcatggt tttcgaaaac      780
ctcgctaaaa cggttctgag caacctgctc gacggcaatc tccagggcat gctgaatatt      840
agccagcatc agtgtgttaa aaaacagtgc ccacagaaca gcggctgctt tcgtcacctg      900
gacgaacgtg aagaatgcaa atgcctgctg aactataaac aggaaggcga caatgcgtt      960 gaaaacccaa acccaacttg caatgaaaac aacggcggct gcgacgctga cgccaaatgc     1020
```

-continued

```
acggaagaag acagcggctc gaatggcaag aaaattacct gcgaatgcac taaaccagac    1080
agctacccac tctttgacgg catttctgc agttaa                               1116
```

<210> SEQ ID NO 5
<211> LENGTH: 371
<212> TYPE: PRT
<213> ORGANISM: Plasmodium falciparum
<220> FEATURE:
<223> OTHER INFORMATION: (FVO) MSP1-42

<400> SEQUENCE: 5

Met Ala His His His His His His Pro Gly Gly Ser Gly Ser Gly Thr
1               5                   10                  15

Ala Val Thr Pro Ser Val Ile Asp Asn Ile Leu Ser Lys Ile Glu Asn
            20                  25                  30

Glu Tyr Glu Val Leu Tyr Leu Lys Pro Leu Ala Gly Val Tyr Arg Ser
        35                  40                  45

Leu Lys Lys Gln Leu Glu Asn Asn Val Met Thr Phe Asn Val Asn Val
    50                  55                  60

Lys Asp Ile Leu Asn Ser Arg Phe Asn Lys Arg Glu Asn Phe Lys Asn
65                  70                  75                  80

Val Leu Glu Ser Asp Leu Ile Pro Tyr Lys Asp Leu Thr Ser Ser Asn
                85                  90                  95

Tyr Val Val Lys Asp Pro Tyr Lys Phe Leu Asn Lys Glu Lys Arg Asp
            100                 105                 110

Lys Phe Leu Ser Ser Tyr Asn Tyr Ile Lys Asp Ser Ile Asp Thr Asp
        115                 120                 125

Ile Asn Phe Ala Asn Asp Val Leu Gly Tyr Tyr Lys Val Leu Ser Glu
    130                 135                 140

Lys Tyr Lys Ser Asp Leu Asp Ser Ile Lys Lys Tyr Ile Asn Asp Lys
145                 150                 155                 160

Gln Gly Glu Asn Glu Lys Tyr Leu Pro Phe Leu Asn Asn Ile Glu Thr
                165                 170                 175

Leu Tyr Lys Thr Val Asn Asp Lys Ile Asp Leu Phe Val Ile His Leu
            180                 185                 190

Glu Ala Glu Val Leu Asn Tyr Thr Tyr Glu Lys Ser Asn Val Glu Val
        195                 200                 205

Lys Ile Lys Glu Leu Asn Tyr Leu Lys Thr Ile Gln Asp Lys Leu Ala
    210                 215                 220

Asp Phe Lys Lys Asn Asn Asn Phe Val Gly Ile Ala Asp Leu Ser Thr
225                 230                 235                 240

Asp Tyr Asn His Asn Asn Leu Leu Thr Lys Phe Leu Ser Thr Gly Met
                245                 250                 255

Val Phe Glu Asn Pro Ala Lys Thr Val Leu Ser Asn Leu Leu Asp Gly
            260                 265                 270

Asn Leu Gln Gly Met Leu Asn Ile Ser Gln His Gln Cys Val Lys Lys
        275                 280                 285

Gln Cys Pro Gln Asn Ser Gly Cys Phe Arg His Leu Asp Glu Arg Glu
    290                 295                 300

Glu Cys Lys Cys Leu Leu Asn Tyr Lys Gln Glu Gly Asp Lys Cys Val
305                 310                 315                 320

Glu Asn Pro Asn Pro Thr Cys Asn Glu Asn Asn Gly Gly Cys Asp Ala
                325                 330                 335

Asp Ala Lys Cys Thr Glu Glu Asp Ser Gly Ser Asn Gly Lys Lys Ile

```
                340                 345                 350
Thr Cys Glu Cys Thr Lys Pro Asp Ser Tyr Pro Leu Phe Asp Gly Ile
        355                 360                 365

Phe Cys Ser
    370
```

<210> SEQ ID NO 6
<211> LENGTH: 17
<212> TYPE: PRT
<213> ORGANISM: Artificial Sequence
<220> FEATURE:
<223> OTHER INFORMATION: Description of Artificial Sequence: Synthetic
      His-6-Tag with non-MSP1-42 peptide linker

<400> SEQUENCE: 6

```
Met Ala His His His His His His Phe Gly Gly Ser Gly Ser Gly Thr
 1               5                  10                  15

Met
```

<210> SEQ ID NO 7
<211> LENGTH: 38
<212> TYPE: DNA
<213> ORGANISM: Artificial Sequence
<220> FEATURE:
<223> OTHER INFORMATION: Description of Artificial Sequence: Synthetic
      PCR primer

<400> SEQUENCE: 7
gggtcggtac catggcagta actccttccg taattgat                            38

<210> SEQ ID NO 8
<211> LENGTH: 48
<212> TYPE: DNA
<213> ORGANISM: Artificial Sequence
<220> FEATURE:
<223> OTHER INFORMATION: Description of Artificial Sequence: Synthetic
      PCR primer

<400> SEQUENCE: 8
ggatcagatg cggccgctta actgcagaaa ataccatcga aaagtgga                 48

<210> SEQ ID NO 9
<211> LENGTH: 23
<212> TYPE: DNA
<213> ORGANISM: Artificial Sequence
<220> FEATURE:
<223> OTHER INFORMATION: Description of Artificial Sequence: Synthetic
      PCR primer

<400> SEQUENCE: 9
taaaaaatat ataaacgaca aac                                            23

<210> SEQ ID NO 10
<211> LENGTH: 23
<212> TYPE: DNA
<213> ORGANISM: Artificial Sequence
<220> FEATURE:
<223> OTHER INFORMATION: Description of Artificial Sequence: Synthetic
      PCR primer

<400> SEQUENCE: 10
aaaagggaag atatttctca ttt                                            23